United States Patent [19]
Nedwin et al.

[11] Patent Number: 5,587,460
[45] Date of Patent: Dec. 24, 1996

[54] 14-BETA-GAL MAMMALIAN LECTINS

[75] Inventors: Glenn E. Nedwin, Half Moon Bay; Timothy S. Bringman, Burlingame, all of Calif.; Pierre-Oliver Couraud, Leperray, France

[73] Assignee: Incyte Pharmaceutical Corporation, Palo Alto, Calif.

[21] Appl. No.: 286,807

[22] Filed: Aug. 5, 1994

Related U.S. Application Data

[63] Continuation of Ser. No. 313,649, Feb. 21, 1989, abandoned, which is a continuation-in-part of Ser. No. 263,734, Oct. 28, 1988, which is a continuation-in-part of Ser. No. 181,747, Apr. 14, 1988, abandoned.

[51] Int. Cl.$^6$ ............ C07K 14/435; C08G 69/26; C12N 15/00
[52] U.S. Cl. ............ 530/396; 530/350; 530/828; 435/172.3
[58] Field of Search ............ 530/350, 396; 435/172.3

[56] References Cited

FOREIGN PATENT DOCUMENTS 60-184020   9/1985   Japan .

OTHER PUBLICATIONS

Parautaud et al DNAS 84: 6345, 1987.
Clerch et al Paochemistry 27: 692, 1988.
Clerch et al Biochem. 27:692–699 1988.
Paietta et al Cancer Res. 48: 280–287 1988.
Hirabayashi et al J. Biochem 101: 987 1987.
Leii et al Eur. J. Immunol. 13: 500–507 1983.
Fudenberg et al Experimental Immunotherapy in Basic & Clinical Immunology p. 756 1984.
Hirabayashi et al., *Biochem. Biophys. Res. Comm.* (1984) 122 (3):938–944.
Gitt et al., *Proc. Natl. Acad. Sci.* (1986) 83:7603–7607.
Abbott et al., "Further studies of oligosaccharide recognition by the soluble 13 kDa lectin of bovine heart muscle ability to accommodate the blood–group–H and –B–related sequences" *Biochem. J.* (1988) 252:283–287.
Abbott et al., "Soluble bovine galactose–binding lectin. cDNA cloning reveals the complete amino acid sequence and an antigenic relationship with the major encephalitogenic domain of myelin basic protein" *Biochem. J.* (1989) 259:283–290.
Abbott et al., "Evidence that the 14 kDa soluble β–galactoside–binding lectin in man is encoded by a single gene" *Biochem. J.* (1989) 259:291–294.
Ali et al., "Isolation and characterization of soluble β–galactoside–binding lectins from mammalian liver" *Biochim. Biophys. Acta* (1989) 992:30–34.
Bardosi et al., "Spatial differences of endogenous lectin expression within the cellular organization of the human heart: A glycohistochemical, immunohistochemical, and glycobiochemical study" *Amer. J. Anat.* (1990) 188:409–418.
Briles et al., "Vertebrate lectins. Comparison of properties of β–galactoside–binding lectins from tissues of calf and chicken" *J. Cell Biol.* (1979) 81:528–537.
Childs et al.,"β–galactoside–binding muscle lectins of man and monkey show antigenic cross–reactions with those of bovine origin" *Biochem. J.* (1979) 183:755–758.
Den et al., "Isolation and properties of β–D–galactoside––specific lectin from chick embryo thigh muscle" *J. Biol. Chem.* (1977) 252:5444–5448.
De Waard et al., "Isolation and properties of β–galactoside binding lectins of calf heart and lung" *J. Biol. Chem.* (1976)251:7581–7587.
Eisenbarth et al., "Lactose sensitive lectin of chick retina and spinal cord" *Biochem. Biophys. Res. Commun.* (1978) 83:1246–1252.
Hirabayashi et al., "Production and purification of a recombinant human 14 kDa β–galactoside–binding lectin" *FEBS Letters* (1989) 250:161–165.
Hirabayashi et al., "Cloning and nucleotide sequence of a full–length cDNA for human 14 kDaβ–galactoside–binding lectin" *Biochim. Biophys. Acta.* (1989) 1008:85–91.
Kajikawa et al., "Release of cytotoxin by macrophages on treatment with human placenta lectin" *Life Sciences* (1986) 39:1177–1181.
Kobiler et al., "Lectin activity from embryonic chick brain, heart, and liver: Changes with development" *Dev. Biol.* (1977) 60:326–330.
Lee et al., "Binding characteristics of galactoside–binding lectin (galaptin) from human spleen" *J. Biol. Chem.* (1990) 265:7864–7871.
Leffler et al., "Multiple soluble lactose binding lectins in rat and mouse intestine" *J. Cell Biol.* (1988) 107:404A (Abstract 2304).

(List continued on next page.)

Primary Examiner—Suzanne E. Ziska
Attorney, Agent, or Firm—Morrison & Foerster

[57] ABSTRACT

Human HL-60 lectin having an amino acid sequence different from other known animal lectins is disclosed. This is one member of a class of mammalian lectins extractable in lactose or detergent and specific for beta-D-galactosides (14-beta-gal lectin which contains at least one glycosylation site). Recombinant methods and materials for production of the mammalian 14-beta-gal lectins, especially HL-60 lectin, in a variety of hosts, and methods to utilize the resulting lectins are also described. Human HL-60 lectin is found in HL-60 cells and in placental tissue.

1 Claim, 19 Drawing Sheets

OTHER PUBLICATIONS

Leffler et al., "Soluble lactose–binding vertebrate lectins: A growing family" *Biochem.* (1989) 28:9222–9229.

Lehmann et al., "An endogenous lectin and one of its neuronal glycoprotein ligands are involved in contact guidance of neuron migration" *Proc. Natl. Acad. Sci. USA* (1990) 87:6455–6459.

Levi et al., "Patterns of expression of a 15k βD–galactoside–specific lectin during early development of the avian embryo" *Development* (1989) 107:909–921.

Lotan et al., "Modulation of galactoside–binding lectins in tumor cells by differentiation–inducing agents" *Cancer Letters* (1989) 48:115–122.

Nowak et al., "Developmentally regulated lectin from embryonic chick pectoral muscle. Purification by affinity chromatography" *J. Biol. Chem.* (1977) 252:6026–6030.

Offner et al., "Recombinant human β–galactoside binding lectin suppresses clinical and histological signs of experimental autoimmune encephalomyelitis" *J. Neuroimmunol.* (1990) 28:177–184.

Powell et al., "Chemical modification of arginine residues of lung galaptin and fibronectin: Effects on fibroblast binding" *Biochem. J.* (1985) 232:919–922.

Powell et al., "The activity of the β–galactoside binding protein of rat lung changes with development" *Fed. Proc. FASEB* (1979) 38:799 (Abstract No. 3005).

Raz et al., "Expression of two different endogenous galactoside–binding lectins sharing sequence honology" *Cancer Res.* (1988) 48:645–649.

Raz et al., "Endogenous galactoside–binding lectins: a new class of functional tumor cell surface molecules related to metastasis" *Cancer and Metastasis Reviews* (1987) 6:433–452.

Regan et al., "Selective expression of endogenous lactose–binding lectins and lactoseries glycoconjugates in subsets of rat sensory neurons" *Proc. Natl. Acad. Sci. USA* (1986) 83:2248–2252.

Teichberg et al., "A β–galactoside binding protein from electric organ tissue of *Electrophorus electricus*" *Proc. Natl. Acad. Sci. USA* (1975) 72:1383–1387.

Vandenbark et al., "A myelin basic protein–specific T lymphocyte line that mediates experimental autoimmune encephalomyelitis" *J. Immunol.* (1985) 135: 223–228.

Wasano et al., "Immunohistochemical localization of 14 kDaβ–galactoside–binding lectin in various organs of rat" *Cell Tissue Res.* (1990) 259:43–49.

Whitney et al., "Oxidation and chemical modification of lung β–galactoside–specific lectin" *Biochem. J.* (1986) 238:683–690.

Zalik et al., "The gastrulating chick blastoderm contains 16–kDa and 14–kDa galactose–binding lectins possibly associated with an apolipoprotein" *Cell Differentiation & Develop.* (1990) 29:217–231.

Zhou et al., "The S–type lectin from calf heart tissue binds selectively to the carbohydrate chains of laminin" *Archives of Biochem. & Biophys.* (1990) 281:27–35.

Leffler et al., "Specificity of binding of three soluble rat lung lectins to substituted and unsubstituted mammalian β–galactosides" *J. Biol. Chem.* (1986) 261:10119–10126.

Levi et al., "Prevention and therapy with electrolectin of experimental autoimmune myasthenia gravis in rabbits" *Eur. J. Immunol.*, (1983) 13:500–507.

Hirabayashi et al., "Human placenta β–galactoside–binding lectin. Purification and some properties" *Biochem. Biophys. Res. Commun.* (1984) 122:938–944.

Lempfrid et al., "Lectin receptor–mediated endocytosis of helix pomatia lectin by zajdela hepatoma cells" *Lectins: Biology, Biochemistry, Clinical Biochemistray, vol. 3. Proceedings of the Fifth Lectin Meeting, Bern, May 31–Jun. 5, 1982*, Bog–Hansen, T. C., et al., eds. Walter de Gruyter, New York (1983) pp. 73–84.

Hirabayashi et al., "Further characterization and structural studies on human placenta lectin" *J. Biochem.* (1987) 101:987–995.

Fudenberg et al., "Experimental Immunotherapy" *Experimental Immunotherapy in Basic & Clinical Immunology* (1987?) Chapter 39, pp. 744–761.

Couraud et al., "Molecular cloning, characterization, and expression of human 14–kDa lectin" *J. Biol. Chem.* (1989) 264: 1310–1316.

```
CTTCTGACAG CTGGTGCGCC TGCCCGGGAA CATCCTCCTG GACTCAAATC ATG GCT      55
                                                       Met Ala
                                                         1

TGT GGT CTG GTC GCC AGC AAC CTG AAT CTC AAA CCT GGA GAG TGC CTT    103
Cys Gly Leu Val Ala Ser Asn Leu Asn Leu Lys Pro Gly Glu Cys Leu
          5                  10                  15

CGA GTG CGA GGC GAG GTG GCT CCT GAC GCT AAG AGC TTC GTG CTG AAC    151
Arg Val Arg Gly Glu Val Ala Pro Asp Ala Lys Ser Phe Val Leu Asn
         20                  25                  30

CTG GGC AAA GAC AGC AAC AAC CTG TGC CTG CAC TTC AAC CCT CGC TTC    199
Leu Gly Lys Asp Ser Asn Asn Leu Cys Leu His Phe Asn Pro Arg Phe
     35                  40                  45                  50

AAC GCC CAC GGC GAC GCC AAC ACC ATC GTG TGC AAC AGC AAG GAC GGC    247
Asn Ala His Gly Asp Ala Asn Thr Ile Val Cys Asn Ser Lys Asp Gly
             55                  60                  65

GGG GCC TGG GGG GGT CAG ACC GAG GCT GTT GCT CCC TTT CAG CCT        295
Gly Ala Trp Gly Gly Gln Thr Glu Ala Val Ala Pro Phe Gln Pro
         70                  75                  80

GGA AGT GTT GCA GAG GTG TGC ATC ACC TTC GAC CAG CAG CTG ACC        343
Gly Ser Val Ala Glu Val Cys Ile Thr Phe Asp Gln Gln Leu Thr
     85                  90                  95

GTC AAG CTG CCA GAT GGA TAC GAA TTC AAG TTC CCC AAC CGC CTC AAC    391
Val Lys Leu Pro Asp Gly Tyr Glu Phe Lys Phe Pro Asn Arg Leu Asn
    100                 105                 110

CTG GAG GCC ATC AAC TAC ATG GCA GCT GAC GGT GAC TTC AAG ATC AAA    439
Leu Glu Ala Ile Asn Tyr Met Ala Ala Asp Gly Asp Phe Lys Ile Lys
    115                 120                 125                 130

TGT GTG GCC TTT GAC TGA AATCAGCCAG CCCATGGCCC CCAATAAAGG            487
Cys Val Ala Phe Asp *
            135

CAGCTGCCTC TGCTCCCCTG                                               507
```

FIG. 1A

14-BETA-GAL MAMMALIAN LECTINS

This application is a continuation of application Ser. No. 07/313,649, filed Feb. 21, 1989 now abandoned, which is a continuation-in-part of Ser. No. 07/263,734, filed Oct. 28, 1988, which is a continuation-in-part of Ser. No. 07/181,747 now abandoned filed Apr. 14, 1988 entitled 14-BETA-GAL MAMMALIAN LECTINS.

TECHNICAL FIELD

The invention relates to the use of carbohydrate-binding proteins as regulators of cell differentiation and immunity. In particular, it concerns a class of lactose- or detergent-extractable mammalian lectins of MW approximately 12–18 kDa which preferably contain a glycosylation site, and a unique 14 kDa lectin from human HL-60 cells and placenta tissue and glycosylated forms of this unique lectin having a MW range of approximately 17–20 kDa, all of which can be recombinantly produced and used in diagnosis and therapy.

BACKGROUND ART

Lectins are defined as proteins which specifically bind carbohydrates of various types, and initial interest was focused on those isolated from plants such as concanavalin A and ricin agglutinin. These lectins, it was found, were useful in protein purification procedures due to the glycosylation state of a number of proteins of interest. Recently, however, interest has focused on a group of lactose-extractable lectins which bind specifically to certain beta-D-galactoside containing moieties and are found in a wide range of mammalian, invertebrate, avian, and even microbial sources. All of the lectins in this class appear to contain subunits of the order of 12–18 kDa and can be readily classified by virtue of a simple diagnostic test—their ability to agglutinate trypsin-treated rabbit red blood cells is specifically inhibited by certain beta-D-galactose-containing moieties. Thus, although the lectins themselves agglutinate trypsinized rabbit erythrocytes, the agglutination can be inhibited by, for example, lactose, thiodigalactoside and other certain beta-D-galactose containing moieties. Other common characteristics include the lack of requirement for metal ions in effecting agglutination, and the requirement for the presence of a reducing agent such as a thiol.

Gitt, M. A., et al. *Proc Natl Acad Sci USA* (1986) 83:7603–7607 obtained two cDNA clones from screening a human hepatoma cDNA library with an antiserum specific to a human lung lectin. These cDNAs encoded proteins similar to those found by a number of other workers in a variety of tissues. For example, Kasai, K., et al. in Japanese Kokai 60/184020 describe a human placental lectin of approximately 14 kDa; the sequence of this lectin was shown by the same group to be somewhat similar to that isolated from chick tissues (Ohyama, Y., et al. *Biochem Biophys Res Commun* (1986) 134:51–56). The chick-derived lectin was shown to be similar in structure to that of discoidin I, which is a lectin observed during the developmental state of the cellular slime mold *Dicytostelium discoideum*.

Caron, M., et al. *Biochim Biophys Acta* (1987) 925:290–296 describe the purification and characterization of similar lectins from rat and bovine brain tissue. deCabutti, N.E.F., et al. *FEBS Letters* (1987) 223:330–334 describe a similar lectin from amphibian ovary. The isolation from eel of a similar "electrolectin" had previously been described by Levi, G., et al. *J Biol Chem* (1981) 256:5735–5740. An additional analogous 14 kDa lectin was produced by cloning and expression of cDNA derived from various murine fibrosarcoma cell lines by Raz, A., et al. *Experimental Cell Research* (1987) 173:109–116. A rat lung 14 kDa lectin, and the cDNA encoding it were described by Clerch, L. B., et al. *Biochemistry* (1988) 27:692–699. Joubert, R., et al. *Develop Brain Res* (1987) 36:146–150 describe the isolation of lectins from rat brain which are capable of agglutinating brain cells. Raz, A., et al. *Cancer Research* (1981) 41:3642–3647 describe a variety of lectins from neoplastic cells of various mammalian species.

A comparison of homologies between several animal lectins including the chick, eel, human placenta, human lung, and two hepatoma-derived lectins (all of these lectins described as referenced above) was set forth by Paroutaud, P., et al. *Proc Natl Acad Sci USA* (1987) 84:6345–6348. It appears that certain amino acid positions of the proteins, including 23, 32, 35, 37, 43, 45, 70, 71, 76, 90, 91, 102, 103, 105, 109–111, are completely conserved in all species compared. Only one lectin of this series, that derived from chicken, contains an "N-linked" glycosylation site, which, however, is not conjugated to saccharide. No mammalian lectin in this family as yet characterized in the art has an N-linked glycosylation site.

Among the soluble lectins, there appear to be a number of varieties with varying molecular weights and/or carbohydrate specificities. Sparrow, C. P., et al. *J Biol Chem* (1987) 252:7383–7390 describe three classes of soluble lectins from human lung, one of 14 kDa, one of 22 kDa, and a third of 29 kDa. All of these are specific to beta-D-galactosides. The carbohydrate specificities of the 14 kDa class are for the most part similar, but the larger molecular weight species tend to have different specificities. Other species are also noted as showing more than one soluble beta-D-galactoside-binding lectin, including mouse (Roff, C. F., et al. *J Biol Chem* (1983) 258:10637–10663); rat (Cerra, R. F., et al. *J Biol Chem* (1985) 260:10474–10477) and chickens (Beyer, E. C., et al. *J Biol Chem* (1980) 255:4236–4239). Among the various beta-D-galactoside-specific soluble lectins, receptor specificity is considerably different, and the approximately 14 kDa group appears distinct from the 22 kDa and 29 kDa representatives described by Sparrow, et al. (supra).

The preferred lectins of the present invention are isolated from the human promyelocytic leukemia cell line HL-60 or human placenta tissue. Lectins have been isolated from the HL-60 cell line by others, but they do not correspond to lectins of this class. Paietta, E., et al. *Cancer Research* (1988) 48:280–287 describe a putatively membrane-bound (not soluble) lectin which recognizes N-acetyl neuramic acid as well as galactose terminating biantennary oligosaccharide structures. The activity is independent of calcium. The apparent molecular weight is 17 kDa. Thus, specificity and solubility status differ abruptly from the lectin protein described herein.

DISCLOSURE OF THE INVENTION

Because the activities of lectins in regulating the immune system and mediating other forms of intercellular communication are so subtle in nature and so critically tuned to the host environment, it is important that a wide range of such regulators be available for therapeutic and diagnostic use. As described in the Background section, a number of members of the class of approximately 14 kDa beta-D-galactose-binding soluble lectins are known in the art. However, while these lectins have properties similar to each other, they are not interchangeable therapeutically or diagnostically. In addition, it appears that if the lectins can be glycosylated, the level and nature of the glycosylation may be manipulated to alter the specificity (e.g., circulating half-life, metabolism in vivo, solubility, stability, or specific activity) of the molecule. The present invention provides a class of lectins which is capable of such manipulation, and also a specific member of this class, all of which enhance the repertoire of therapeutic and diagnostic tools. The invention also provides recombinant materials and methods to produce these specific new members of the repertoire.

In one aspect, the invention is directed to a 14 kDa beta-D-galactoside-binding mammalian lectin (14-beta-gal lectin) which preferably contains at least one glycosylation site. In another aspect, the invention is directed to a 14-beta-gal mammalian lectin which consists essentially of the amino acid sequence shown as amino acids 2–135 in FIG. 1. The amino acid at position 1, methionine, is usually removed when the protein is produced recombinantly in mammalian cells, and may be removed when the protein is produced recombinantly in bacterial cells, and is not present naturally, and is not essential for activity. In another aspect the invention is directed to HL-60 and placenta derived lectins of MW 14 kDa and glycosylated forms thereof in the range of MW 17–20 kDa.

In other aspects, the invention is directed to DNA sequences encoding the 14-beta-gal mammalian lectins, which lectins are capable of N-linked glycosylation, and in particular the protein of FIG. 1, or other HL-60 or human placenta derived lectins of this class, in isolated and purified form, and/or ligated to heterologous control sequences suitable for recombinant expression. In a further aspect, the invention is directed to host cells transformed with the DNA sequences described herein, and to methods to produce the desired lectin proteins. It is also directed to antibodies specifically reactive with the lectins of the invention.

BRIEF DESCRIPTION OF THE DRAWINGS

FIG. 1A shows the cDNA sequence and deduced amino acid sequence of both the HL-60 and placenta lectin. Superscript numbers correlate to the corresponding nucleotides and boxes show start and stop codons. The asterisk indicates the possible N-linked glycosylation site.

MODES OF CARRYING OUT THE INVENTION

A. Definitions

It is known, in general, that proteins may exist in a variety of essentially equivalent forms including the acidic and basic salts thereof, forms which are derivatized at side-chain functional groups, forms associated with lipids and membranes, and other modifications made through post-translational processing of the cell expressing the DNA encoding the desired lectin. All of the proteins defined below are inclusive of these various forms.

Figure 1B:
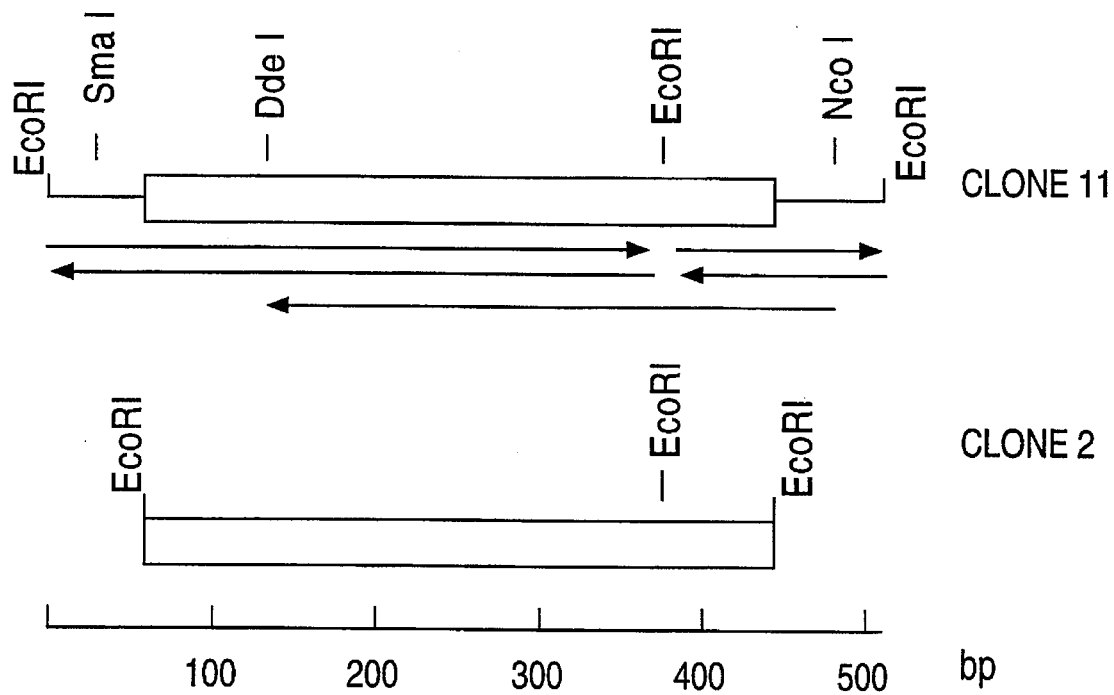
FIG. 1B shows restriction maps of two HL-60 cDNA clones with the coding region indicated by open boxes and the sequencing strategy used.

As used herein, "HL-60 lectin" refers to a lectin of the class defined below and includes lectins from HL-60 cells as well as lectins from human placenta tissue. One embodiment consists essentially of the amino acids shown in FIG. 1A numbered from 2–135 which contain at least one tripeptide sequence, Asn-X-Thr or Asn-X-Ser, which provides a glycosylation site. It is believed that even in native production by HL-60 cells and placenta tissue, the N-terminal methionine of the HL-60 lectin is cleaved, and the remaining protein may be acetylated. Various forms of post-translational processing can be expected depending on the cell producing the protein, and the resultant processed proteins are, of course, included within the scope of the invention.

In particular, it should be noted that unlike the analogous mammalian lectins whose protein sequences are known, the HL-60 lectin preferably contains a glycosylation site, Asn-Leu-Thr, starting at position 96. The native material apparently does not, at least in part, contain glycosylation at this site; however, when appropriately produced in other recombinant hosts, the site can be glycosylated. Accordingly, glycosylated forms, so long as the glycosylation does not destroy activity, are included within the invention.

It should also be further noted that the embodiment of "HL-60 lectin" as shown in FIG. 1A contains more cysteine residues (6) than other known homologous animal lectins. The present invention is not so limited, and may contain any number of cysteine residues or no cysteine residues, so long as activity is retained.

"HL-60 lectin" further includes the peptide comprising positions 2–135 in FIG. 1A or the naturally occurring mutants or allelic variations thereof. It is well understood that proteins produced by organisms do not necessarily remain stable in the form studied, but that the genes encoding them are subject to natural mutations and variations; these are therefore included in the invention.

It is at present unknown whether HL-60 lectin, when produced in its native environment of HL-60 cells or placental tissue, is secreted as such, or whether it is a soluble or protein-associated cytoplasmic protein of the cytoplasm or nucleus of the cell. The HL-60 lectin can be produced to ensure secretion by recombinant addition of a known signal sequence. The recovery of the protein from the medium is, of course, simpler than recovery that requires cell lysis.

It is shown herein that HL-60 cells and placenta tissue produce 14 kDa beta-gal binding lectin.

The "HL-60 lectins" described above are representative of the class of 14-beta-gal mammalian lectins preferably having at least one glycosylation site and claimed herein. As used herein, the phrase "14-beta-gal mammalian lectin containing at least one glycosylation site" refers to a class of peptides having the characteristics of the group of lectins exemplified by the HL-60 lectin of FIG. 1 which contain at least one tripeptide sequence, Asn-X-Thr or Asn-X-Ser, which provides a glycosylation site. However, as stated previously, the present invention includes 14-beta-gal mammalian lectins without glycosylation sites.

To be included in the class of 14-beta-gal mammalian lectins containing at least one glycosylation site, a peptide must exhibit the biological properties of this class enumerated as follows: a molecular weight when nonglycosylated of approximately 14 kDa, as a practical matter about 12–18 kDa when measured. The lectin must be capable of binding certain beta-D-galactoside containing moieties (i.e., beta lactose), and specifically must cause hemagglutination of trypsinized rabbit erythrocytes in standard lectin assays, wherein the agglutination is inhibited by certain moieties containing the beta-lactose galactoside linkage, such as lactose and thiodigalactoside. The requirements for ability to cause hemagglutination includes presence of a reducing agent capable of maintaining thiol groups and tryptophan residues in the reduced form, but the activity is independent of metal ions. Typically, peptides of the invention which have this activity show extensive homology to the animal lectins referenced in the Background section above, with the additional requirement that there be at least one glycosylation site.

It is preferred that the lectins have at least 40% homology with the HL-60 lectin of FIG. 1A, preferably 75% homology, and most preferably over 90% homology. The preferred location of the glycosylation site is at residues 96–99 as is the case for the lectin of FIG. 1A, or within, at most, a 4 amino acid spacing upstream or 3 amino acid spacing downstream, i.e., between residues 92 and 101 inclusive. Other preferred locations include those which contain Asn, X (any amino acid), and Ser/Thr residues in any of the animal lectins at nonconserved regions.

Particularly preferred embodiments are peptides with at least 95% homology with the known mammalian lectins referenced above wherein, however, unlike the native forms, at least one glycosylation site is included in the sequence. In these preferred embodiments, also, the preferred position for the glycosylation site is positions 96–99 or at least between positions 92–101 inclusive. The most preferred embodiment of the 14-beta-gal lectins containing glycosylation sites is the HL-60 lectin of FIG. 1A (whether based on HL-60 cell sources or placental tissue sources and the naturally occurring mutants and allelic variants thereof).

B. Isolation of HL-60 Lectin-Encoding cDNA.

a. From HL-60 Cells

HL-60 cells, ATCC CCL240, were cultured for 40 hours in the presence of DMSO. The cells were then lysed, the mRNA isolated using standard techniques, and a cDNA library constructed in lambda-GT10 according to the method of Huynh, T. V., et al, *DNA Cloning I*, D. M. Glover, Ed., R. L. Press (1985) pp. 49–78. The library was probed with two sets of 14-mer probes designated

LP59: 3'-CTTAAATTTAAAGG-5'
        C   G   C   G and

LP60: 3'-CTAAAATTTTAATT-5'.
        G   G   C   G
                        T

These probes were designed on the basis of known lectin sequences, specifically those of conserved regions near the C-terminus. They encode the amino acid sequences Glu-Phe-Lys-Phe-Pro (which occurs in HL-60 lectin at positions 106–110) and Asp-Phe-Lys-Ile-Lys (which occurs in HL-60 lectin at positions 126–130). The probes were labeled at their ends with $^{32}$P using T4 polynucleotide kinase and [gamma-$^{32}$P]ATP.

Phage colonies were screened by hybridizing LP59 with duplicate nitrocellulose filters which were prehybridized for 2–4 hours at 37° C. Hybridization buffer contained 6×SSC, 20 mM phosphate buffer pH 7, 2 ×Denhardt's solution, 0.1% SDS, 2 mM EDTA, and 100 mcg/ml yeast RNA. Filters were then washed in 4×SSC at room temperature.

Out of approximately $10^6$ phage colonies, 17 positive clones were found which hybridized to LP59; 9 of these also hybridized with the LP60 probe. All 9 clones contained an internal EcoRI site providing a "short" and a "long" fragment. Dideoxy sequencing of three of the clones hybridizing with both probes showed identical DNA sequences differing only in 5' and 3' extensions of the open-reading frame.

The 507 bp sequence determined for one of these clones is shown in FIG. 1A. The open reading frame of 405 base pairs (clone 11) encoding a protein of 135 amino acids with a theoretical molecular weight of 14,744 daltons is shown. As calculated without the N-terminal methionine, the protein has a theoretical molecular weight of 14,613. This protein is homologous to other animal 14-beta-gal lectins such as rat lung lectin. Homologies with other known animal lectin protein sequences range from 40% (mouse hepatoma) to 96% (human lung peptides).

b. From Human Placental Tissue

A human placenta cDNA library was constructed from human placenta poly(A$^+$) RNA in lambda-GT10 as described by Tarantino, A. L., et al., *Biochemistry* (1985) 24:4665–4671 using a synthetic primer complimentary to the 3'untranslated region, nucleotides 486–502 of the HL-60 cDNA clone 11(3'TCCGTCGACGGAGACGA 5') rather than oligo dT to prime the first strand cDNA synthesis. The library was screened with a labeled 311 bp fragment of HL-60 (clone 2) (FIG. 1B) containing most of the lectin coding sequence but none of the 3' untranslated primer sequence. Four positive clones were isolated using the probe as described for HL-60 library screening.

It is apparent from the deduced amino acid sequence that a glycosylation site Asn-Leu-Thr is present at positions 96–98 of the FIG. 1A HL-60 lectin. This is the first known mammalian lectin which contains a glycosylation site, and its presence offers the opportunity to potentially alter the carbohydrate binding capability, solubility, circulating half life, metabolism in vivo, stability, or specific activity of the lectin without destroying its ability to bind to beta-D-galactoside compounds.

Furthermore, the availability of the DNA sequence shown in FIG. 1A, as well as the cDNA sequences for other mammalian lectins described in the Background Art section above provides the opportunity to manipulate the gene so that a glycosylation site can be provided even though none is present natively. Hence, in one approach to preparing the preferred embodiments of the invention, a tripeptide sequence between positions 92–101 can be converted by site-specific mutagenesis to a glycosylation site. The provision of a glycosylation site at this position would not be expected to destroy the 14-beta-gal lectin activity of the peptide.

In an alternate approach, the retrieved HL-60 and placenta cDNA can be manipulated to provide additional homology to 14-beta-gal lectin sequences from other sources, but at the same time retaining the sequence encoding the glycosylation site.

C. Characteristics of the Genomic and cDNA

Figure 2A:
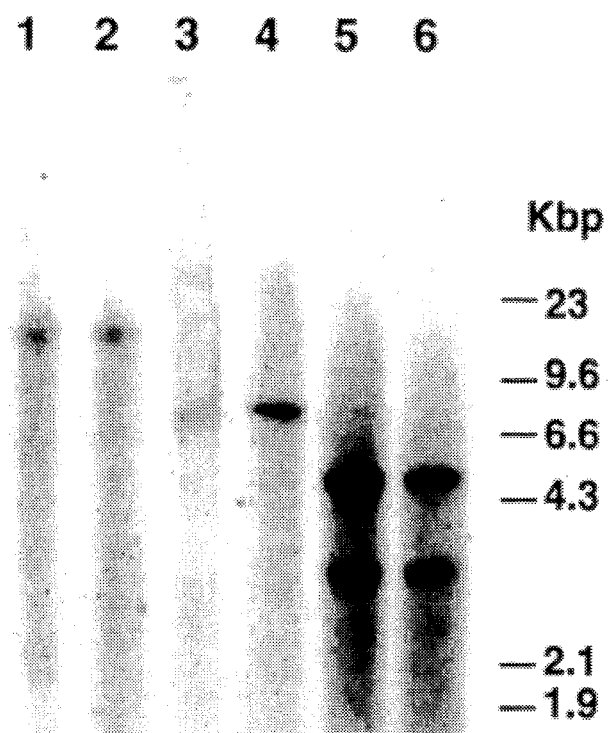
FIG. 2A shows a Southern blot of DNA from HL-60 and human placenta cells probed with HL-60 cDNA indicating one gene for the 14 kDa lectin.

Southern blots of human genomic DNA isolated from HL-60 cells and human placenta tissue were performed after digestion with BamHI, HindIII, or EcoRI and probed the 445 bp SmaI/NcoI fragment of HL-60 cDNA clone 2 (FIG. 1B) as seen in FIG. 2A. For DNA digested with HindIII (lane 1, placenta, lane 2, HL-60) or BamHI (lane 3, placenta, lane 4, HL-60), there was one hybridizing band of approximately 7.5 or 15 kbp; digestion with EcoRI (lane 5, placenta, lane 6, HL-60) yielded two hybridizing bands of 5.1 and 3.2 kbp, consistent with an internal EcoRI site.

Figure 2B:
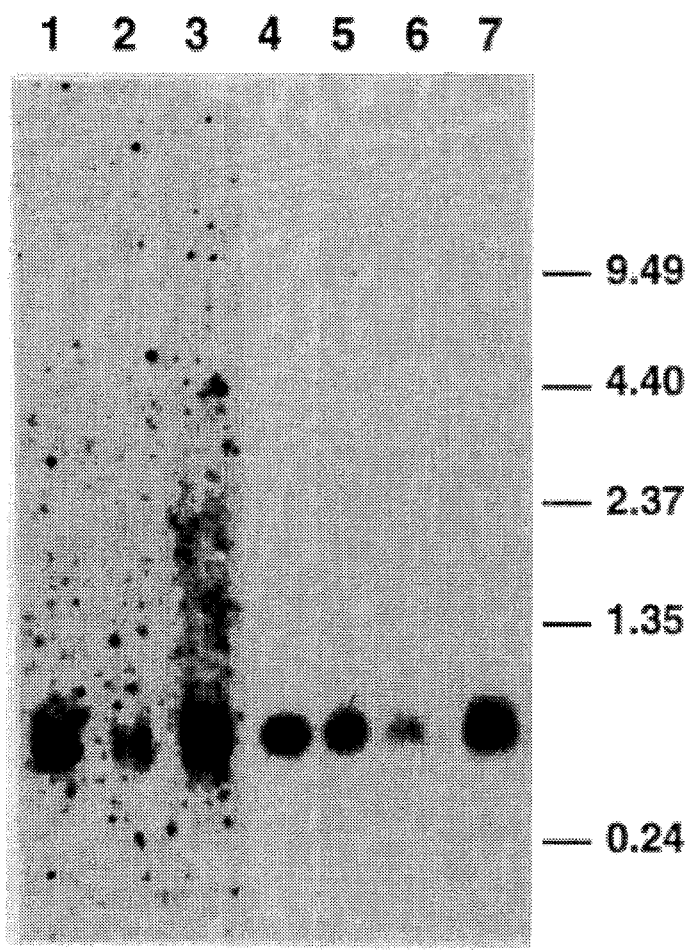
FIG. 2B shows a Northern blot probed with the HL-60 cDNA indicating that the mRNA messages contained in a variety of cell lines putatively encoding lectins are the same length and homologous.

Northern blots, FIG. 2B, using mRNA preparations from HL-60 cells (lanes 1, 5, and 6), normal human placenta (lane 3), human SK hepatoma cells (ATCC CCL24601) (lane 4), human erythroleukemia leukemia KG-1A cells (ATCC HTB 52) (lane 7), and human choriocarcinoma JEG-3 cells (ATCC HTB 36) (lane 2) probed with a 311 bp EcoRI cDNA fragment of clone 2 (FIG. 1B) showed one hybridization band of approximately 700 nucleotides, indicating similar or identical length mRNA messages for all cells surveyed.

D. Antibodies Reactive with the Inventive Lectins

The lectins of the invention can be used in conventional ways to raise antisera reactive with, and specific for, these lectins. An antibody "specific for" HL-60 lectin means an antibody which is immunoreactive with this lectin, or with proteins encoded by the naturally occurring mutations and allelic variants of its gene, but not immunoreactive with other lectins. Because of the extensive homology of the FIG. 1A HL-60 lectin with other lectins of the 14-beta-gal class, not all of the antibodies raised against HL-60 lectin will in fact be specific to it. However, by producing monoclonal antibodies to the HL-60 lectin, specific antibodies can be generated. In addition antibodies specific for various glycosylated forms can also be prepared.

Similarly, antibodies can be prepared which are specific for any particular member of the 14-beta-gal lectins with, or without, at least one glycosylation site, of the invention, both in nonglycosylated and especially in glycosylated forms.

In short, the antibodies within the scope of the invention are those monoclonal lines which are reactive with one or more members of the lectins of the invention, but not cross-reactive with the lectins presently known in the art. Also included in the scope of the invention are antisera raised by any of the lectins of the invention, since these antisera will be unique to these lectins, even if they contain, in some measure, cross-reactive antibodies with known lectins.

E. Recombinant Production of HL-60 Lectin

The cDNA encoding the amino acid sequence of FIG. 1A or synthetic or semi-synthetic variants thereof or encoding the 14 kDa HL-60, can be used for the recombinant production of HL-60 lectin in a variety of systems. Suitable DNAs encoding the alternate 14-beta-gal lectins, such as those containing at least one glycosylation site can also be expressed recombinantly. The lectin-encoding DNA is mobilized by ligating the appropriate intronless sequence to control sequences regulating expression, transfecting the resulting expression systems into appropriate hosts, and culturing the transformed or transfected hosts under conditions favorable for the expression of the DNA. Genomic DNA encoding the HL-60 and placenta lectin and its naturally occurring mutants and allelic variants can be recovered from the HL-60 or placenta genome using the cDNA as a probe. This genomic DNA can also be used in eucaryotic systems capable of processing introns. The lectin-encoding sequence can be ligated into the expression system preceded by an ATG to obtain the lectin as a mature protein. Alternatively, signal sequences known to be operable in the intended host, such as the penicillinase and alkaline phosphatase system in bacteria, the alpha-factor system in yeast, or various hormone signal sequences in mammalian cells can be used to effect secretion by constructing the expression system with the DNA encoding signal in reading phase with the lectin DNA. The lectin could also be produced as a fusion protein by ligating the coding sequence into reading frame with an additional coding sequence if desired.

A variety of host systems with appropriate controls are by now well known in the art. For example, among procaryotic hosts, *E. coli* are preferred, although other species, such as *Bacillus, Pseudomonas*, or other bacterial strains could be used. Suitable control systems include promoters associated with bacterial proteins such as the beta-lactamase and lactose (lac) promoter systems (Chang et al. *Nature* (1977) 198:1056; the tryptophan (trp) promoter system (Geoddel et al. *Nucleic Acids Res.* (1980) 8:4057) and the lambda-derived $P_L$ promoter and N-gene ribosome binding site system (Shimatake et al. *Nature* (1981) 292:128). This list provides the most commonly used promoters in procaryotes and is by no means all inclusive.

Similarly, a variety of vectors and promoters is known for yeast systems including the promoter for 3-phosphoglycerate kinase (Hitzeman et al. *J Biol Chem* (1980) 255:2073); the enolase gene promoter (Holland, M. J., et al. *J Biol Chem* (1981) 256:1385) or the leu2 gene obtained from YEp 13 (Broach, J., et al. *Gene* (1978)

For expression in cells of higher organisms, promoters operable in such cells include viral promoters such as the SV40 promoter (Fiers et al. *Nature* (1978) 273:113) or promoters derived from adenovirus, bovine papilloma virus, Rous sarcoma virus, and so forth. Also usable are regulatable promoters such as the metallothionein I or metallothionein II promoters. Control sequences for retroregulation are also available such as that associated with the crystal protein gene of B. thuringgiensis. Currently available also are systems for production of recombinant proteins in insect cells and in plant cells, although plant cell systems are currently less convenient. Their inconvenience, however, is a result of the current state of the art, and not of an inherent incompatibility between this host cell system and the gene encoding the proteins of the invention.

The appropriate coding sequences are ligated to the control sequences in operable configuration and in suitable vectors for transfection into the intended host. The vectors may commonly include plasmids, virus particles or phage depending on the intended host and the mode of transformation. "Transformation", as used herein, includes all forms of causing uptake of foreign DNA by a host cell including viral infection, transduction, conjugation or, probably most common, induction of uptake in vitro by transfection using transfecting agents such as calcium chloride or DEAE/dextran, depending on the host.

The transformed cells are then screened for those which contain the desired DNA and the successful transformants are cultured under conditions which affect the expression of the coding sequences. The lectin produced is then purified from the medium (if the construction results in secretion) or from the lysed cells (if the construction results in an intracellular protein).

In either case, the lectin is purified by standard methods, including extraction in lactose solution, or other (Triton X-100), followed by chromatographic procedures. A convenient chromatographic procedure includes chromatography on lactose Sepharose gels. In this approach, the extract is loaded onto the gel, the gel is washed and elution is conducted by supplementing the equilibration buffer with 100 mM lactose either in batch or gradient form. The presence of the protein in the active fractions can be easily detected by the ability of the fraction, after removal of lactose, to cause hemagglutination of trypsinized rabbit erythrocytes, wherein said hemagglutination is inhibited by millimolar concentrations of beta lactose or thiodigalactoside.

STATEMENT OF UTILITY

The lectins of the invention are useful in a range of therapeutic and diagnostic applications. In a manner analogous to that demonstrated for electrolectin by Levy, G., et al. *Eur J Immunol* (1983) 13:500–507 the 14 -beta-gal mammalian lectins with glycosylation site(s) herein can be used in the treatment of autoimmune diseases such as myasthenia gravis. Other autoimmune diseases which are subject to treatment by these lectins include rheumatoid arthritis, systemic lupus erythomatosis, juvenile diabetes, and multiple sclerosis.

Since these proteins are immune system regulators, they are also useful in the prevention of graft vs. host disease and inhibition of rejection of transplants in general. In addition, antibodies prepared which are immunoreactive with these proteins are useful in diagnosis of tumors since the levels of these lectins on the cell surface are correlated with metastatic cancer. The lectins are also useful in drug delivery applications by causing the homing of the drug to suitable targets when conjugated to the lectin. The lectins of the invention can also be used as a targeting agent when coupled to certain cytotoxic molecules.

For use in therapeutic applications, the protein is formulated in a manner suitable for its mode of administration using formulation technology known in the art and described, for example, in *Remington's Pharmaceutical Sciences*, latest edition, Mack Publishing Co., Philadelphia, Pa. Typical formulations for injection include admixture with physiological buffer for injection such as Hank's solution or Ringer's solution, encapsulation in liposomes or other emulsifying agents suited for drug delivery, and the like.

The dosage level and manner of administration of the lectins of the invention will depend on the indication and the subject, as well as the severity of the condition to be treated. Preferred dose levels range from about 0.004 mg/kg/day to about 2 mg/kg/day. Preferred methods of administration include intravenous, subcutaneous, and oral methods.

The following examples are intended to illustrate, but not to limit the invention.

EXAMPLE 1

Expression of the HL-60 Lectin cDNA in Mammalian Cells to Give Intracellular Protein Plasmid pHL11 was constructed by ligating the insert of the LP59/LP60 hybridizing clone from the lambda gt10 library described above into a bacterial cloning vector. Thus, pHL11 contains the entire coding sequence and the 5' and 3' untranslated regions.

The gene is ligated into the expression vector plasmid p171 in two segments. Plasmid 171 contains an expression system for murine DHFR and an SV40 promoter and polyadenylation site separated by a polylinker containing HindIII and BamHI restriction sites.

The 5'portion of the HL-60 lectin sequence is cloned by digesting pHL11 with EcoRI and SmaI and ligating the fragment into EcoRI/SmaI digested pUC13, replicating in *E. coli* to give pL1. The downstream portion is amplified by digesting pHL11 with NcoI, blunt ending with Klenow, digesting with EcoRI, isolating a 140 bp EcoRI/blunt fragment and ligating this fragment into EcoRI/SmaI digested pUC13, and amplifying in *E. coli* to give pL2.

The upstream fragment is isolated from pHL1 by digesting with HindIII and EcoRI and isolating the 370 bp fragment; the downstream EcoRI/BamHI 150 bp fragment is isolated from pHL2. The isolated fragments are ligated into the BamHI/HindIII cleaved expression vector p171 and the ligation mixture transformed into *E. coli* and selected for successful transformants. The plasmid containing the HL-60 lectin gene under control of the SV40 promoter and polyadenylation sites, pSV/HL-60, was isolated. The isolated vector was then used to transform a Chinese hamster ovary (CHO) cell line which lacks DHFR, and successful colonies capable of growth in F12 media lacking glycine, hypoxanthine, and thymidine were isolated and expanded in selective media.

The selected cells were then inoculated at $2 \times 10^6$ cells/ml of F12 medium for 48 hr, and harvested. The cells were lysed and the lysate confirmed to contain HL-60 lectin using the rabbit erythrocyte agglutination assay.

EXAMPLE 2

Expression of the HL-60 Lectin cDNA in Mammalian Cells to Produce Secreted Protein A ClaI restriction site was introduced immediately upstream of the codon for amino acid 1 of FIG. 1 preserving the initiation codon and maintaining the downstream coding sequence. This upstream sequence was removed by digestion with ClaI/EcoRI and isolated as a 310 bp ClaI/EcoRI fragment. This, along with a 150 bp EcoRI/BamHI fragment isolated from pHL2 above and containing the downstream fragment were ligated to ClaI/BamHI digested expression vector which contains a hydrophobic secretory protein signal sequence under control of the SV40 promoter, and a ClaI site at the 3'end of the signal. This expression vector also contains an expression system for murine DHFR.

The ligation mixture was transformed into DHFR deficient CHO cells as described above, and cultured as in Example 1. After 48 hr in F12 (gHT-) medium, the culture medium was harvested and assayed for HL-60 lectin production using an ELISA.

EXAMPLE 3

Isolation of HL-60 Lectin from HL-60 Cells

Native HL-60 lectin was isolated from HL-60 cell lysate as follows: the protein was solubilized from the lysate by treating with lactose or Triton X-100 solution and the solubilized lectin was purified by affinity on lactose Sepharose or asialofetuin Sepharose columns.

Protein-containing fractions from the elution gradient of lactose Sepharose show peaks when subjected to SDS-PAGE at both 14 kDa and 17 kDa which show the appropriate lectin activity. Protein—containing peaks from asialofetuin Sepharose columns contain a lectin of 14 kDa and a minor species at 30 kDa. Lectin isolated from human placenta subjected to similar treatment shows a major 14 kDa peak and a minor species at 30 kDa regardless of the affinity column and no 17 kDa species.

Figure 3:
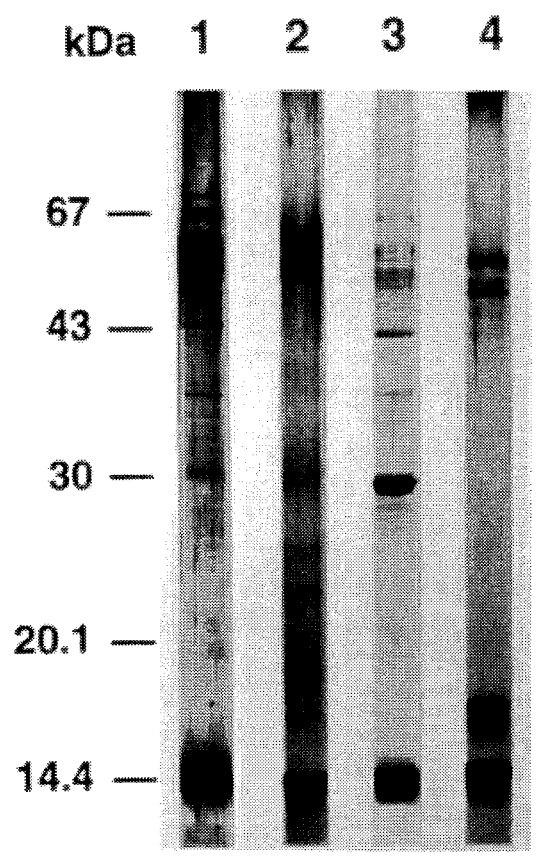
FIG. 3 shows SDS-PAGE of purified lectin preparation.
Figure 4A:
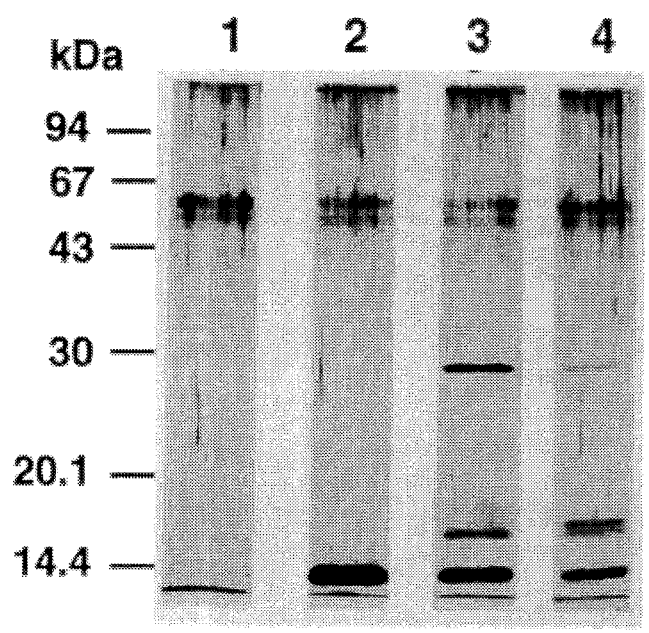
FIG. 4A shows HPLC purification of HL-60 lectin and SDS-PAGE of the eluate fractions.
Figure 4B:
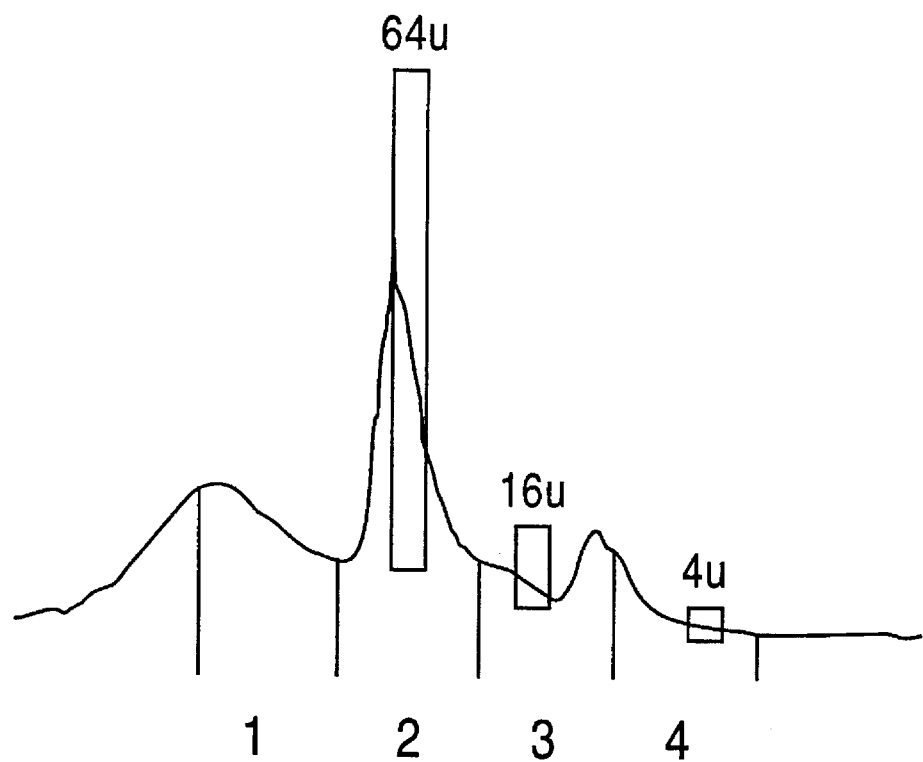
FIG. 4B shows agglutinating activity of each fraction superimposed over absorbance at 214 nm.

Following affinity chromatography, the HL-60 lectin is purified to homogeneity using a C4 HPLC column using an acetonitrile/water-TFA solvent system. FIGS. 3 and 4 show the result of gradient elution in acetonitrile/TFA and SDS-PAGE analysis of the fractions. The 14 kDa lectin appears in fraction 2 as shown by the SDS-PAGE results.

The determination of which of the 14 kDa and 17 kDa proteins were responsible for hemagglutinating activity was accomplished by HPLC analysis of HL-60 protein eluted fractions from lactose-Sepharose affinity chromatography. While the 14 kDa lectin was separated from the 17 kDa protein, fractions containing the 17 kDa species also included substantial amounts of the 14 kDa lectin. As seen in FIG. 4, the 14 kDa protein corresponds to the peak of hemagglutination activity. Further, Western blot analysis of the 14 kDa and 17 kDa proteins using rabbit antisera raised against purified 14 kDa placenta lectin showed a cross-immunoreactivity with the 14 kDa protein but not with the 17 kDa lectin (see FIG. 5).

Figure 5:
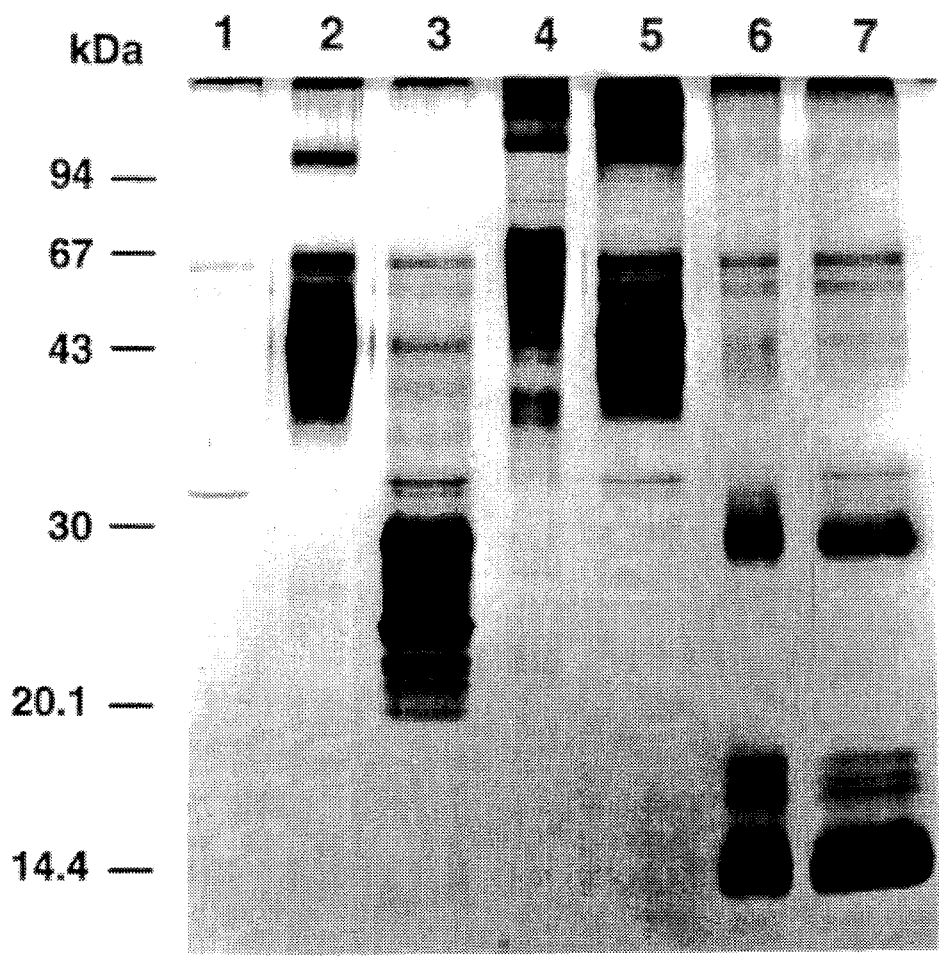
FIG. 5 shows silver-stained SDS-PAGE analysis of HL-60 lectins treated with N-glycanase.

The possibility that the 17 kDa protein is a glycosylated form of the 14 kDa protein was tested by treatment of the proteins with N-glycanase (Genzyme), which hydrolyzes N-asparagine-linked oligosaccharides from glycoproteins. Purified lectin samples (2 mcg) were dissolved in 10 mcl of 0.5% SDS-0.1M 2-mercaptoethanol, and treated with 0.15 units of N-glycanase. As seen in FIG. 5, the enzyme had no effect on any of the HL-60 proteins under conditions where the orosomucoid and fetuin glycoproteins were deglycosylated. Lane 1 contains N-glycanase; lane 2, human orosomucoid; lane 3, orosomucoid and N-glycanase; lane 4, bovine fetuin; lane 5, bovine fetuin and N-glycanase; lane 6, HL-60 lectin purified on lactose Sepharose; and lane 7, HL-60 lectin and N-glycanase. Because the observed molecular weight for the 14 kDa lectin almost matches the predicted molecular weight, 14,613 daltons, it is unlikely that the 14 kDa lectin is glycosylated.

Purified 14 kDa and 17 kDa HL-60 proteins were amino acid sequenced after SDS-PAGE. Blockage of the amino terminal end of the 14 kDa lectin necessitated treatment of the lectin with cyanogen bromide to cleave the lectin at an internal methionine. The amino acid sequence of that fragment was identical to the sequence of a 14 residue C-terminal fragment of 14 kDa placenta lectin derived from cleavage of a methionine at position 121. While the 17 kDa HL-60 protein was also blocked at the N-terminus, the cyanogen bromide fragment yielded a unique amino acid sequence unrelated to the 14 kDa HL-60 protein. This fragment further did not show any significant homology with any other proteins of the Swiss Protein Data Bank.

Thus, the 17 kDa protein is not affected by N-glycanase, is not responsible for hemagglutination activity, does not react with polyclonal antibodies specific for the 14 kDa placenta lectin (see FIG. 6, infra) and its amino acid sequence differs greatly from that of the 14 kDa sequence.

EXAMPLE 4

Isolation of Lectin from Human Placenta Tissue

Fresh or frozen human placenta was homogenized in 3 volumes (ml/gr) of homogenizing buffer and the homogenate centrifuged at 10,000×g for 15 minutes. The resulting pellet was then suspended in 2 volumes of homogenizing buffer (relative to the original tissue weight) and 0.1 M beta-lactose, stirred 1 hour at 4° C., and centrifuged at 10,000×g for 1 hour. Solid ammonium sulfate was then added to the resulting supernatant to 50% saturation and the solution was incubated at 4° C. for 3 hours. The solution was then centrifuged at 30,000×g for 15 minutes, the pellet was discarded, and solid ammonium sulfate was added to the supernatant to saturation. The resulting solution was then incubated 16 hours at 4° C., centrifuged at 30,000×g for 1 hour, and the resulting pellet was dissolved in 1/10 volume (relative to the original tissue weight) of 10 mM Tris-1 mM EDTA pH 7.5 and dialyzed against homogenizing buffer. The resulting lectin was purified by affinity on lactose Sepharose or asialofetuin columns.

EXAMPLE 5

Expression of HL-60 Lectin cDNA in *E. coli* Cells

An expression vector for use in *E. coli* was constructed from vector pKK223-3 (Pharmacia) containing the isopropyl thiogalactoside (IPTG) inducible trp-lac (tac) promoter. Lectin cDNA was mutagenized at the 5' end of the coding sequence by oligonucleotide-directed mutagenesis via the Bio-Rad Muta-Gene M13 Kit to introduce a ClaI restriction site close to the lectin ATG codon. The synthetic oligonucleotide used had the sequence:

5'-CTCCTGGACTC<u>ATCGAT</u>GGCTTGTGGT-3'
ClaI

The 421 bp ClaI/NcoI fragment of the mutagenized lectin cDNA of clone 11 (FIG. 1B) was blunted and ligated using T4 DNA ligase to a blunted EcoRI site in the vector. *E. coli* JM101 were transformed by standard methods and the resulting clones were tested by hybridizing with a lectin cDNA probe. Clone structure was confirmed by restriction site analysis. Clones which tested positive by hybridization were selected and grown in large culture.

In order to express the lectin cDNA, 500 ml of LB medium were inoculated with 2.5 ml of an overnight culture of *E. coli* JM101 transformants. After 90 minutes, the cells were induced by addition of 1 mM IPTG and grown for 6.0 hours at 37° C. Cells were then harvested and washed in 25 ml of 20 mM Tris-HCl, pH 7.4, 2 mM EDTA, 150 mM NaCl, 4 mM 2-mercaptoethanol, and 1 mM PMSF. The cells were then lysed twice by sonication for 5 minutes each and the cell lysate was clarified by centrifugation at 25,000×g for 10 minutes.

The lectin-containing supernatant was purified by affinity chromatography using a column comprising beta-lactose coupled to vinyl sulfone activated Sepharose and eluted with 0.1M beta-lactose in homogenizing buffer. All fractions obtained were analyzed by SDS-PAGE, immunoblotting, and hemagglutination activity using standard methods. N-terminal amino acid sequence analysis showed an N-terminal alanine indicating that the bacteria processes the protein by cleaving the initial methionine. It is also understood that the N-terminal alanine can be modified such as by acetylation.

Figure 6:
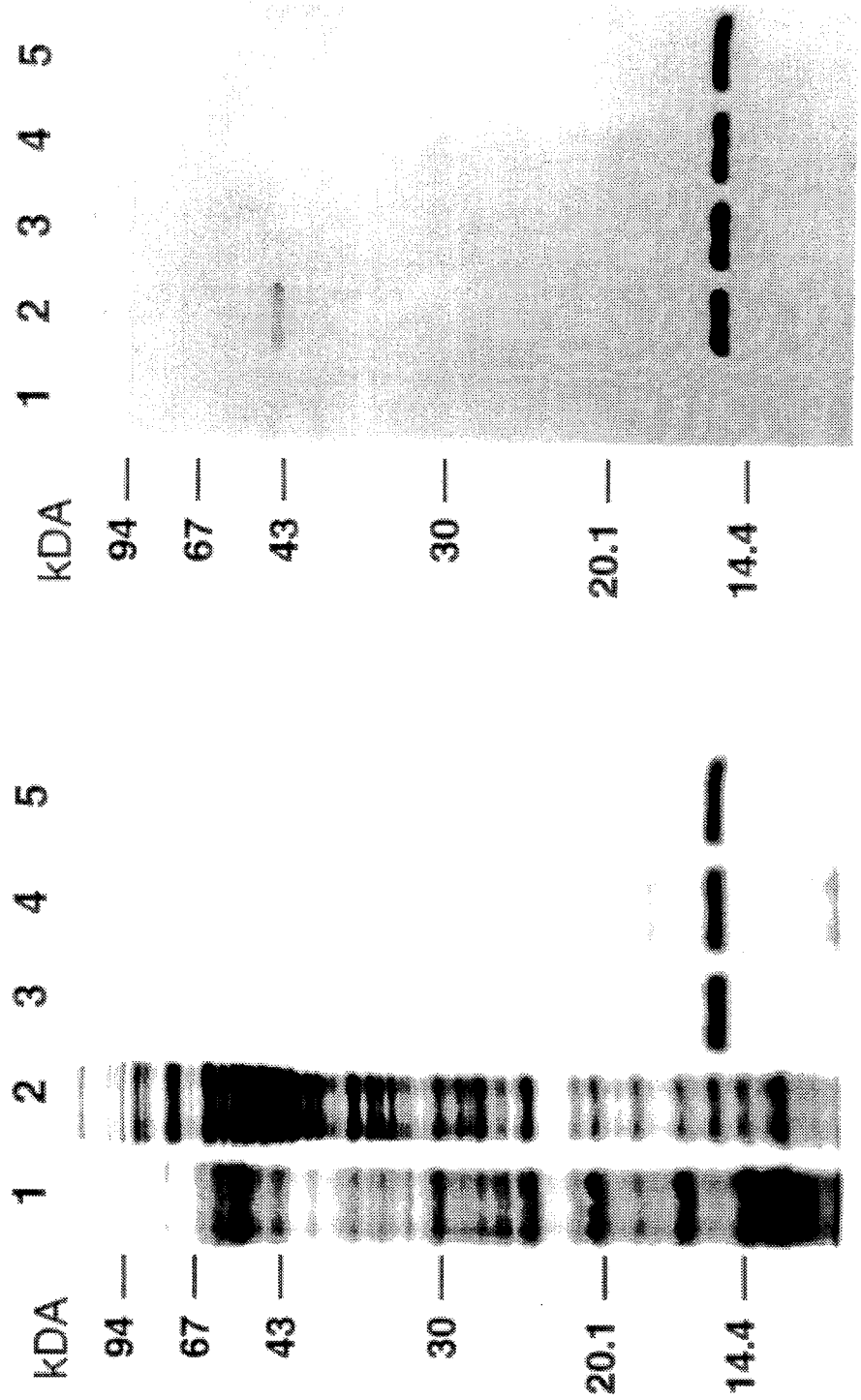
FIGS. 6A and 6B show SDS-PAGE and Western blot analysis of various 14 kDa lectins including that derived from E. coli cells, transfected with lectin cDNA.

Western blot analysis of the purified *E. coli* lectin revealed that the lectin had the same electrophoretic mobility and immunoreactivity as placenta and HL-60 lectins. FIG. 6 shows SDS-PAGE and Western blot analysis of several 14 kDa lectins. In panel A the lectins were subjected to electrophoresis and stained with Coomassie blue R-250; in panel B, the lectins were transferred to a PVDF membrane and then visualized by treatment with anti-placenta lectin antibodies and HRP-conjugated goat anti-rabbit IgG.

Lanes for both panels are: Lane A1, 50 mcg JM101 *E. coli* lysate; lane A2, 50 mcg lysate from *E. coli* containing an HL-60 lectin expression plasmid; lane A3, 5 mcg placenta lectin, and lane A4, 5 mcg HL-60 lectin; lane A5, 5 mcg *E. coli*-derived lectin; lane B1, 10 mcg JM101 lysate; lane B2, 10 mcg lysate from *E. coli* containing an HL-60 lectin expression plasmid; lane B3, 0.2 mcg placenta lectin; lane B4, 0.2 mcg HL-60 lectin; lane B5, 0.2 mcg *E. coli*-derived lectin. Additionally, the *E. coli*-derived lectin subjected to hemagglutinin assay showed similar activity as HL-60 and placenta lectins.

Figure 12:
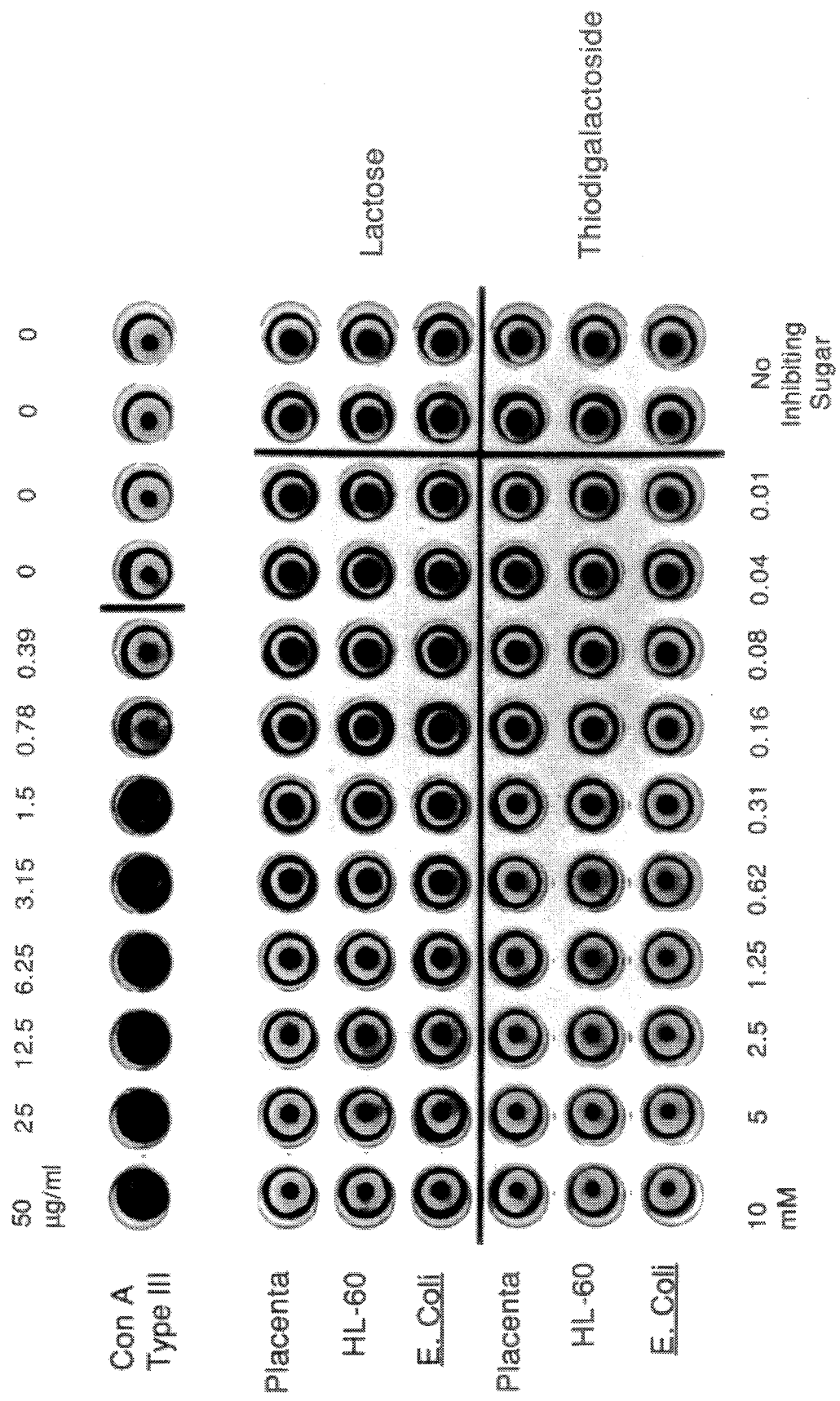
FIG. 12 shows results of hemagglutinin bioassay of purified lectins from human placenta, HL-60 cells and E. coli cells transfected with vectors containing lectin cDNA and an operably linked secretion signal, and inhibition of agglutination by sugars.

Assay of the *E. coli*-derived lectin as well as the HL-60 and placenta lectins revealed the *E. coli* expressed lectin had approximately the same specific activity as placenta and HL-60 lectins (FIG. 12, infra). The foregoing demonstrates that the recombinant lectin is biologically active and similar to lectins isolated from natural sources such as HL-60 cells and placenta.

EXAMPLE 6

Figure 7:
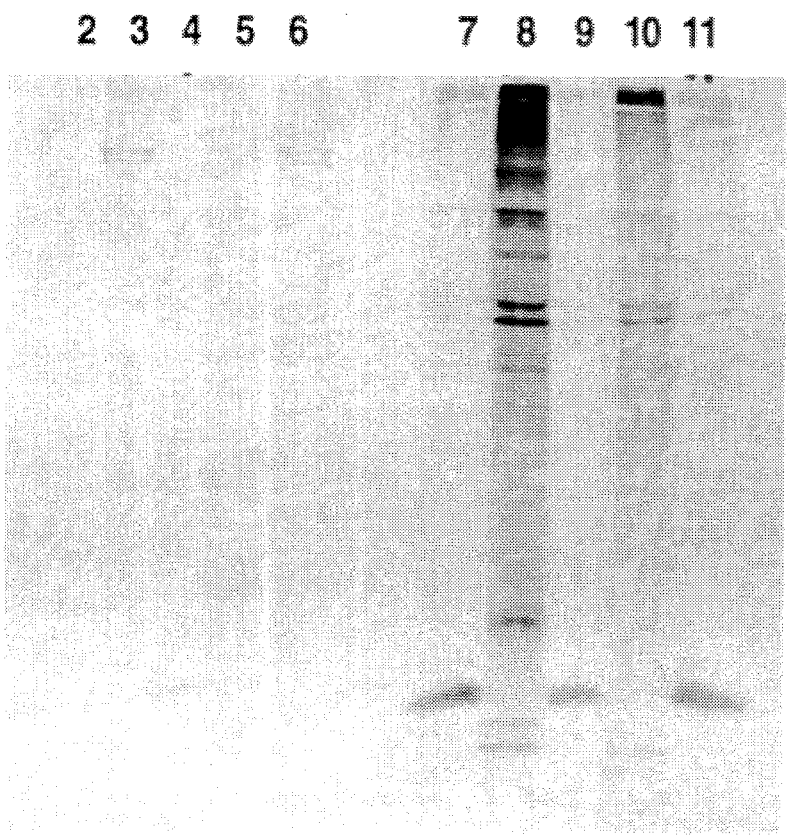
FIG. 7 shows SDS-PAGE analysis of immunoprecipitated metabolically labeled HL-60/placenta lectins produced by CHO cells transfected with HL-60 lectin cDNA or HL-60 lectin cDNA and an operably linked secretion signal.

Expression of HL-60 Lectin Gene in CHO Cells to Give Intracellular or Secreted Protein CHO cells were transfected with vectors containing lectin cDNA (cDNA vector) or with lectin cDNA and an operably linked secretion signal (secretion vector). FIG. 7 shows SDS-PAGE analysis of immunoprecipitated metabolically labeled lectins produced by CHO cells transfected and treated as set forth below. Lane 2 contains supernatant of P-18 (cDNA vector) transformed cells plus inmmune serum; lane 3 contains P-18 supernatant plus normal rabbit serum (NRS); lane 4 contains PS-2 (lectin secretion vector) supernatant, immune serum, and N-glycanase; lane 5 contains PS-2 supernatant and immune serum; lane 6 contains PS-2 supernatant and NRS; lane 7 contains PS-2 extract and immune serum; lane 8 contains PS-2 extract and NRS; lane 9 contains PS-2 extract, immune serum, and N-glycanase; lane 10 contains P-18 extract and NRS; and lane 11 contains P-18 extract and immune serum.

Several species of the lectin, 18-20 kDa forms and the 14 kDa species, were immunoprecipitated. As seen in lane 5, the large form of the lectin is secreted only by cells transfected with cDNA operably linked to a secretion signal, yet is not found in cell lysates (lane 7). The large forms of the lectin are converted to the 14 kDa species when treated with N-glycanase (lane 4).

Figure 8:
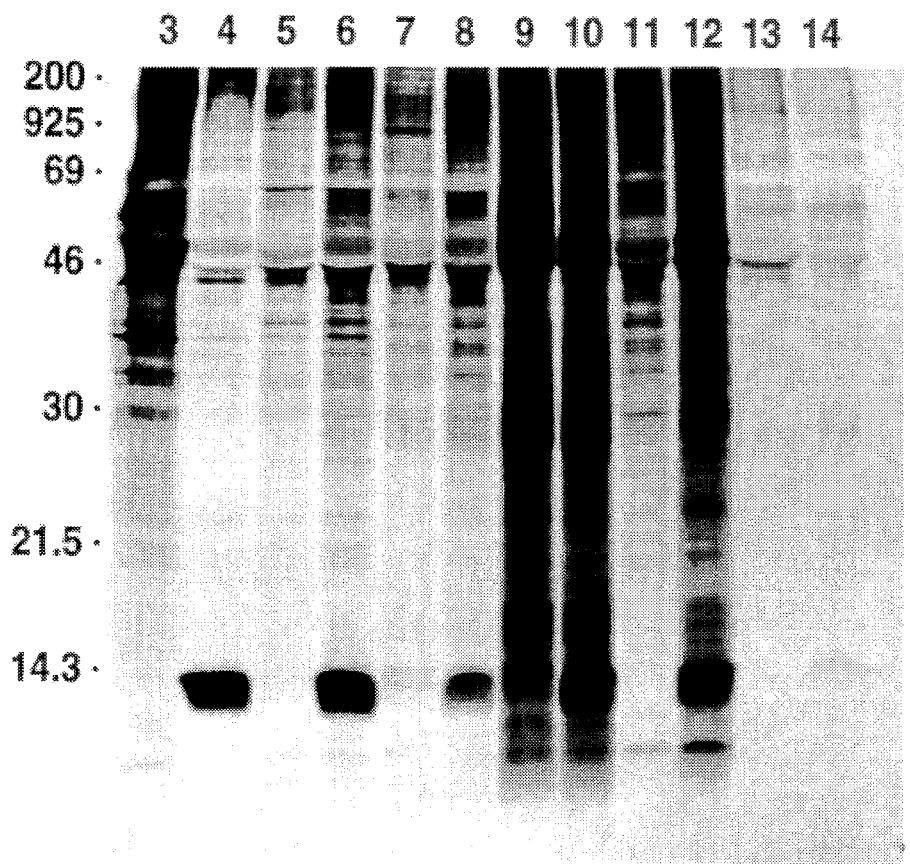
FIG. 8 shows SDS-PAGE analysis of immunoprecipitated metabolically labeled lectin from several cell lines.

SDS-PAGE analysis of immunoprecipitated metabolically labeled lectin from lysates of several other cell lines is shown in FIG. 8. Lanes 3 and 4 contain lectin from human foreskin fibroblast lysate treated with NRS and immune serum, respectively; lanes 5 and 6 contain lectin from lysate of transfected CHO cells treated with NRS and immune serum, respectively; lanes 7 and 8 contain lectin from lysate of HL-60 cells treated with NRS and immune serum, respectively; lanes 9 and 10 contain lectin from lysate of U937 cells treated with NRS and immune serum, respectively; lanes 11 and 12 contain lectin from KGla cell lysate treated with NRS and immune serum, respectively; and lanes 13 and 14 contain lectin from lysate of PBL cells treated with NRS and immune serum, respectively. Only a 14 kDa form of lectin is present in cell lysate, consistent with the findings shown in FIG. 7. Immunoprecipitation of supernatants fail to show any secreted lectin.

Figure 9:
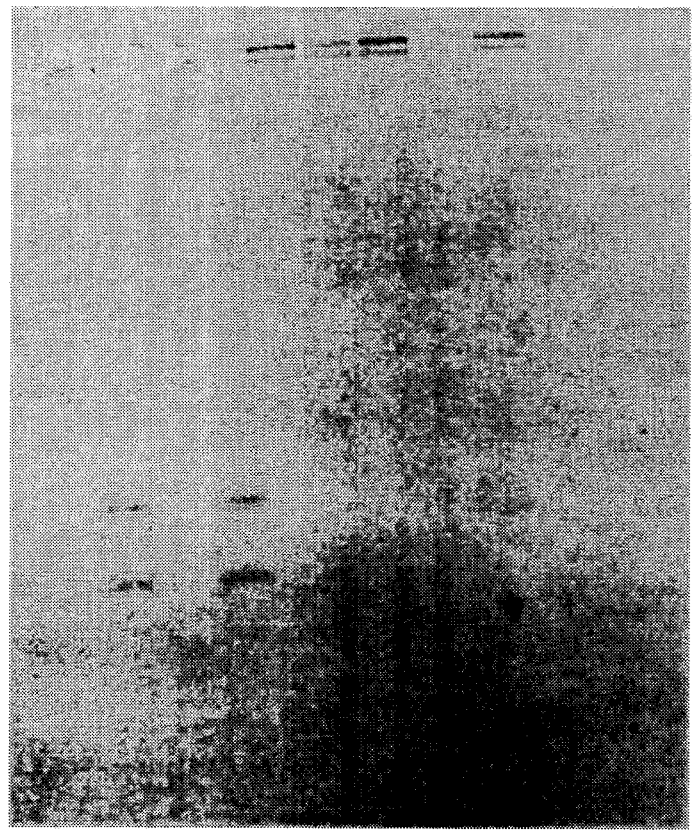
FIG. 9 shows SDS-PAGE analysis of immunoprecipitated lectin secreted by CHO cells transfected with HL-60 lectin cDNA operably linked to a secretion signal.

In FIG. 9 there is shown SDS-PAGE analysis of immunoprecipitated metabolically labeled lectin secreted by CHO cells transfected with lectin cDNA operably linked to a secretion signal. Lanes 1 and 2 contain PS-2 (lectin secretion vector) supernatant and NRS or immune serum, respectively; lanes 3 and 4 contain PS-2 supernatant, 200 ng/ml lectin and either immune serum or NRS, respectively. Lanes 2 and 3 show secretion of 14 kDa and 18 kDa species.

Figure 10:
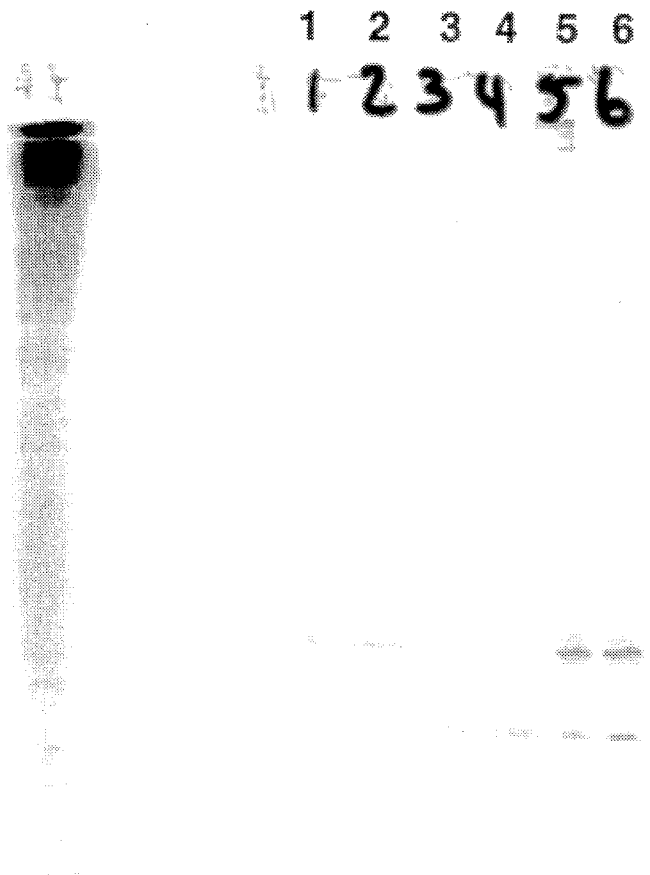
FIG. 10 shows SDS-PAGE analysis of immunoprecipitated lectin secreted by CHO cells transfected with HL-60 lectin cDNA operably linked to a secretion signal and treated with N-glycanase.

Lectins secreted by CHO cells transfected with lectin cDNA operably linked to a secretion signal were treated with N-glycanase and subjected to SDS-PAGE and the results are shown in FIG. 10. Lanes 1, 2, 5, and 6 contain PS-2 (lectin secretion vector) supernatant and immune serum, and lanes 3 and 4 contain PS-2 supernatant treated with N-glycanase. The absence of the 18–20 kDa lectins in lanes 3 and 4 indicates that the 18–20 kDa lectins are the glycosylated form of the 14 kDa lectin.

Figure 11:
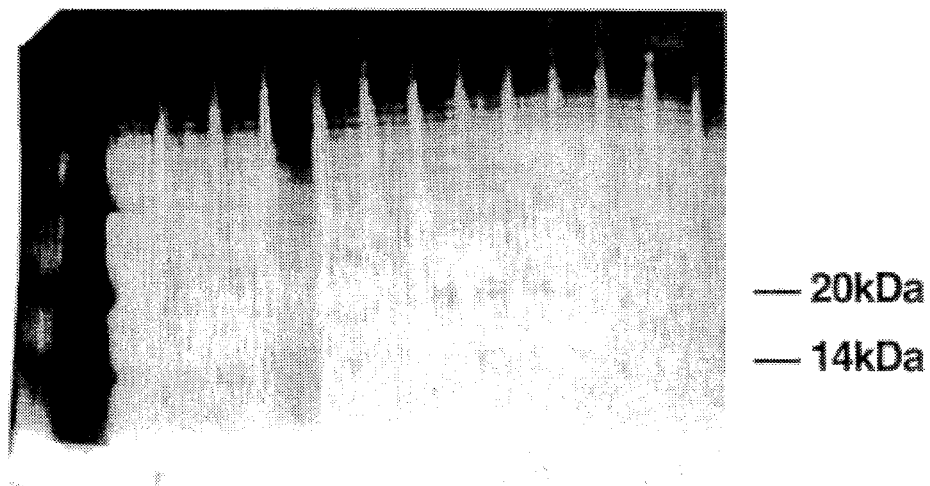
FIG. 11 shows lactose Sepharose purification of lectins secreted by CHO cells transfected with HL-60 lectin cDNA operably linked to a secretion signal and SDS-PAGE of the eluate fractions.

Lectins secreted by CHO cells transfected with lectin cDNA operably linked to a secretion signal were purified on a lactose Sepharose column and the elution fractions subjected to SDS-PAGE. As seen in FIG. 11, both the large and small forms of lectin bind to lactose and are active in an agglutination assay as shown in the following example.

EXAMPLE 7

Assay for Beta-galactoside Binding Activity of Lectins

Biological activity of 14 kDa lectin from HL-60 cells, placenta tissue, and *E. coli* cells transfected with lectin cDNA operably linked to a secretion signal was ascertained by agglutination of trypsinized rabbit erythrocytes. As seen in FIG. 12, the top row shows a Concanavalin A control with an agglutination end-point at 1.5 mcg/ml. The lower 6 rows show the three purified 14 kDa lectins incubated with varying concentrations of competing sugars beta-lactose and thiodigalactoside which are known to be potent inhibitors of the 14 kDa placenta lectin. Thiodigalactoside inhibited agglutination of the erythrocytes at concentrations greater than 0.31 mM and beta-lactose inhibited agglutination at concentrations greater than 1.25 mM.

EXAMPLE 8

Effect of HL-60 Lectin on the Primary Humoral Immune Response Against Proteins and Polysaccharides in Two Different Mouse Strains A. Immunization of Mice with Acetylcholine Receptor from Torpedo Marmorata, Tetanus Toxoid, and Capsular Polysaccharides The acetylcholine receptor from the electric organ of the ray Torpedo marmorata was purified by affinity chromatography on *Naja naja siamensis* neurotoxin. Tetanus toxoid was obtained from the Swedish National Bacteriological Laboratory and consisted of formalin-treated tetanus toxin (normally used for vaccination). A mixture of capsular polysaccharide extracts from 23 different serotypes of *Streptococcus pneumoniae* was obtained from Merck Sharp Dome, Inc. (Pneumovax®).

Young adult female BALB/c and C56BL/6 mice (2–4 months of age) were used. Mice were injected subcutaneously with 10 mcg of purified acetylcholine receptor, tetanus toxoid or pneumococcal polysaccharide in Freund's complete adjuvant without and with HL-60 lectin. The amount of injected lectin in these preliminary experiments was between 0.1 and 25 mcg per mouse.

Blood was obtained after 3 days and after 1, 2, 3 and 4 weeks. To follow the development of experimental autoimmune myasthenia gravis in mice injected with acetylcholine receptor, the mice were observed daily for signs. of neuromuscular dysfunction and after 10 days subjected to forced exercise using repetitive grasping, swimming and inverted hang. These exercises were repeated after warming under a heat lamp at 35° C. for 5 min. The results of these observations are presented in Table 1 and show that in both strains of mice tested at higher dose levels, recombinant HL-60 lectin had a marked beneficial effect on slowing neuromuscular dysfunction.

TABLE 1

Clinical Signs of Neuromuscular Dysfunction in Mice Injected with Acetylcholine Receptor With and Without Lectin

| Mouse Strain | BALB/c (Percent of mice in each experimental group showing clinical signs of disease) | C57B/6 (%) |
|---|---|---|
| Lectin 0.1–5 mcg + receptor | 25 | 68 |
| Lectin 15–25 mcg + receptor | 4 | 11 |
| Receptor only | 18 | 59 |

After the observation period, the animals were sacrificed, skinned and eviscerated and cholinergic receptor extract was prepared from the whole carcasses.

B. Determination of the Amount of Free Receptor in Mice Immunized with Acetylcholine Receptor Known portions of receptor extracts as prepared in this Example, Part A, were incubated with a tenfold excess of $^{125}$I-alpha-bungarotoxin for 1 hour at 37° C. so as to label the receptor for quantitation. The mixture was subjected to gel filtration on Sephacryl G200 to separate free and bound toxin. The amounts of receptor present in the mouse carcasses is shown in Table 2 together with the amount of recombinant HL-60 lectin coadministered. These data show that at doses of about 15–25 mcg recombinant HL-60 lectin counteracted the in vivo effects of the injected acetylcholine receptor.

TABLE 2

Muscle Acetylcholine Receptor Content in Mice Immunized with Acetylcholine Receptor With and Without Lectin (Determinations Made 10 Days After Injection)

| | Carcass Content (mol × 10$^{-11}$) | Complexed with Ig (%) |
|---|---|---|
| Normal mice | 3.9 ± 0.7 | 0 |
| AChR + lectin (0.1 mcg) | 0.8 ± 0.4 | 48 ± 6.0 |
| AChR + lectin (1 mcg) | 1.4 ± 0.3 | 52 ± 2.0 |
| AChR + lectin (5 mcg) | 0.9 ± 0.5 | 44 ± 5.0 |
| AChR + lectin (15 mcg) | 3.5 ± 0.4 | 11 ± 10.7 |
| AChR + lectin (25 mcg) | 3.2 ± 0.6 | 11 ± 7.8 |
| AChR only | 1.5 ± 0.2 | 65 ± 2.6 |

C. Determination of Receptor-Bound IgG and IgM Antibodies Against Torpedo and Mouse Receptor These determinations were performed by incubating receptor extract with a tenfold excess of labeled bungarotoxin overnight at 4° C., followed by separating the precipitates, washing, and counting the radioactivity. The Table 2 results show that in lectin-treated mice, doses of approximately 15–25 mcg were effective in reducing the amount of muscle acetylcholine receptor complexed with immunoglobulin (Ig).

D. B-Cell Repertoire of Mice Immunized with the Acetylcholine Receptor Tetanus Toxoid and Pneumococcal Polysaccharide 1. Preparation of Primary Clones of Monoclonal Antibodies from Immunized BALB/c Mice Three BALB/c female mice (7–8 weeks old) were injected intraperitoneally with 5 mcg of receptor antibody, tetanus toxoid or pneumococcal polysaccharide, respectively, in complete Freund's adjuvant and 2 weeks later intravenously with the same amount of antigen in 0.15M sodium phosphate buffer, pH 7.4. Three mice of the same strain were immunized with these antigens in combination with 15 mcg of HL-60 lectin. The animals were sacrificed 4 days after the booster injection and spleen cells ($10^8$ cells) were fused with the nonsecreting B-lymphocytoma cell line SP2-OAg14 ($2 \times 10^9$ cells), and the cell mixture was distributed in 6×96 Costar tray wells ($2 \times 10^5$ cells/well) with a feeder layer of mouse peritoneal macrophages ($5 \times 10^5$ cells/well). From the third day in culture HAT (hypoxanthine-aminopterin-thymidine) medium was added.

After 10–14 days, supernatants were assayed for binding to the respective antigens used for immunization. An ELISA was used as described above. The results in Table 3 show that when lectin is administered with antigens there is a reduction of the B cell repertoire producing specific antibodies to the administered protein antigens after primary immunization.

TABLE 3

Number of Clones Producing Antibodies Against Torpedo Receptor, Tetanus Toxoid and Pneumococcal Polysaccharide Hybridomas (180 Primary Clones for Each Antigen) Derived From BALB/c Mice Injected with the Antigens With and Without HL-60 Lectin (15 mcg)

|  | Antigen + Lectin | Antigen Only |
|---|---|---|
| Torpedo receptor | 54 | 129 |
| Tetanus toxoid | 79 | 161 |
| Pneumococcal polysaccharide | 111 | 143 |

EXAMPLE 9

Effect of HL-60 Lectin on Primary Immune Response

A. Determination of Antibodies Against Torpedo Acetylcholine Receptor

Microtiter wells were coated overnight with 100 mcl of a solution containing 5 mcg/ml of purified receptor as prepared in Example 8, Part A, and incubated with serum (diluted 1/25) for 3 hours at 37° C. After washing, the plates were incubated for 3 hours at 37° C. with alkaline phosphatase-conjugated goat anti-mouse immunoglobulins. The plates were then washed extensively and incubated for 1 hour at 37° C. with p-phenylphosphate ethanolamine buffer. The reaction was stopped by addition of 25 mcl of 3M NaOH, and the binding of the labeled antibody was measured in an ELISA microreader at 405 nm. A normal mouse serum pool from more than 50 mice served as negative control. The cut-off limit was the mean +4SD of cumulated values obtained with this normal serum pool. The results were compared to results obtained by radioimmunoassay and expressed in moles toxin receptor precipitated by 1 liter of serum, after subtraction of the mean +4SD of cumulated results from a normal population (more than 50 mice).

B. Antibodies Against Mouse Acetylcholine Receptor

The antibodies were determined using as antigen a complex between a partially purified normal mouse skeletal muscle receptor and $^{125}$I-alpha-bungarotoxin. The results were expressed in moles toxin receptor precipitated by 1 liter of serum, after subtraction of the mean +4SD of cumulated results from a normal population (more than 50 mice).

C. Antibodies Against Tetanus Toxoid and Capsular Polysaccharides

The antibodies were determined in an enzyme-linked immunosorbent assay (ELISA). Microtiter wells were coated overnight with 100 mcl of a solution containing 5 mcg/ml of the antigen and incubated with serum (diluted 1/200) for 3 hours at 37° C. After washing, the plates were incubated for 3 hours at 37° C. with alkaline phosphatase-conjugated goat anti-mouse immunoglobulins. The plates were then washed extensively and incubated for 1 hour at 37° C. with p-phenylphosphate ethanolamine buffer. The reaction was stopped by addition of 25 mcl of 3M NaOH, and the binding of the labeled antibody was measured in an ELISA microreader at 405 nm. A normal mouse serum pool from more than 50 mice served as negative control. The cut-off limit was the mean +4SD of cumulated values obtained with this normal serum pool. The values were expressed in milliabsorbance units after subtraction of the mean +4SD of the normal serum pool.

Groups of BALB/c mice were immunized with tetanus toxoid, pneumococcal polysaccharide, ray Torpedo receptor and mouse receptor without added HL-60 lectin and with antigen plus various levels of HL-60 lectin.

Figure 13A:
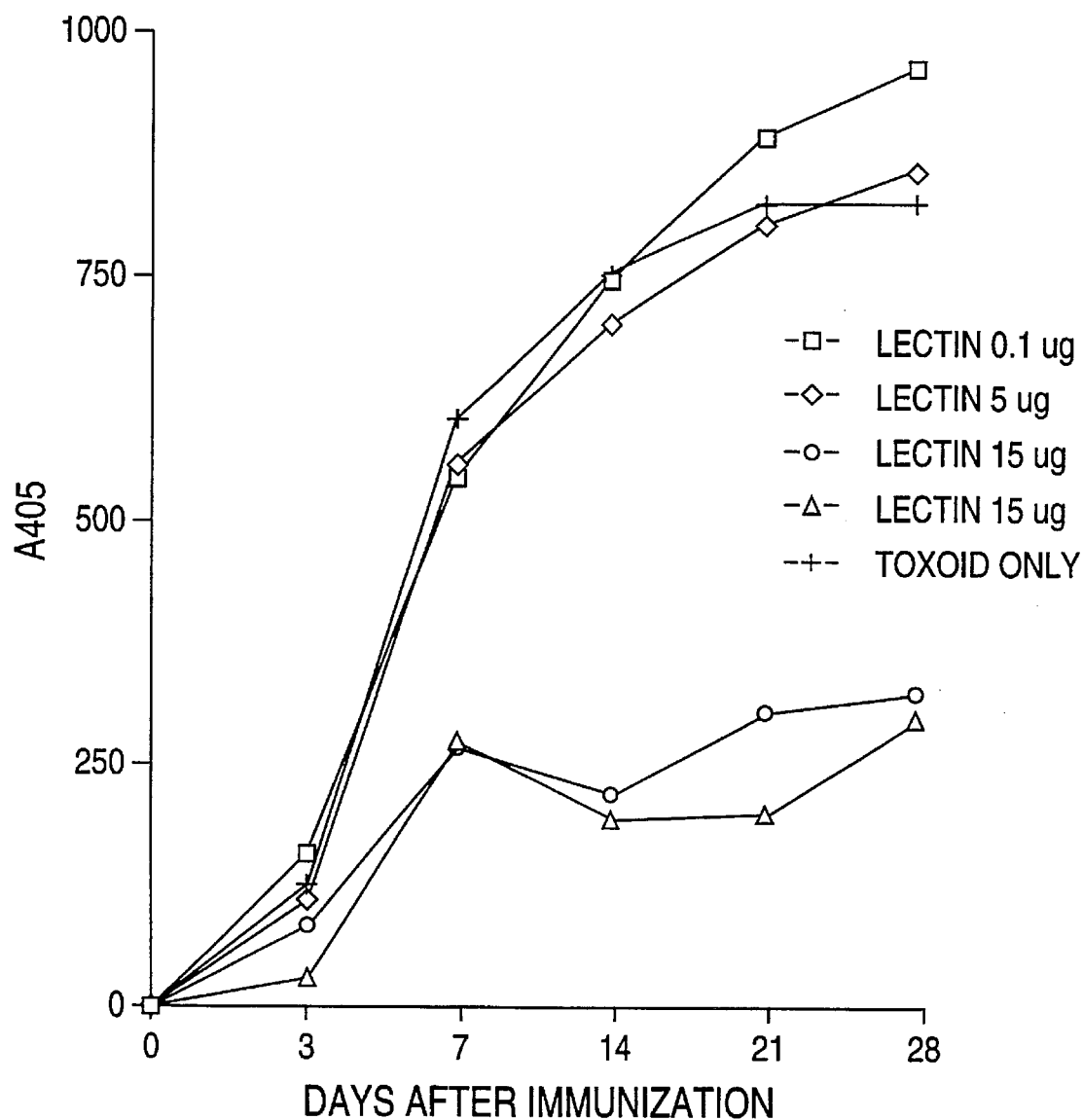
FIGS. 13A, 13B, 13C and 13D are graphs which show the effect of HL-60 lectin on primary immune response.
Figure 13B:
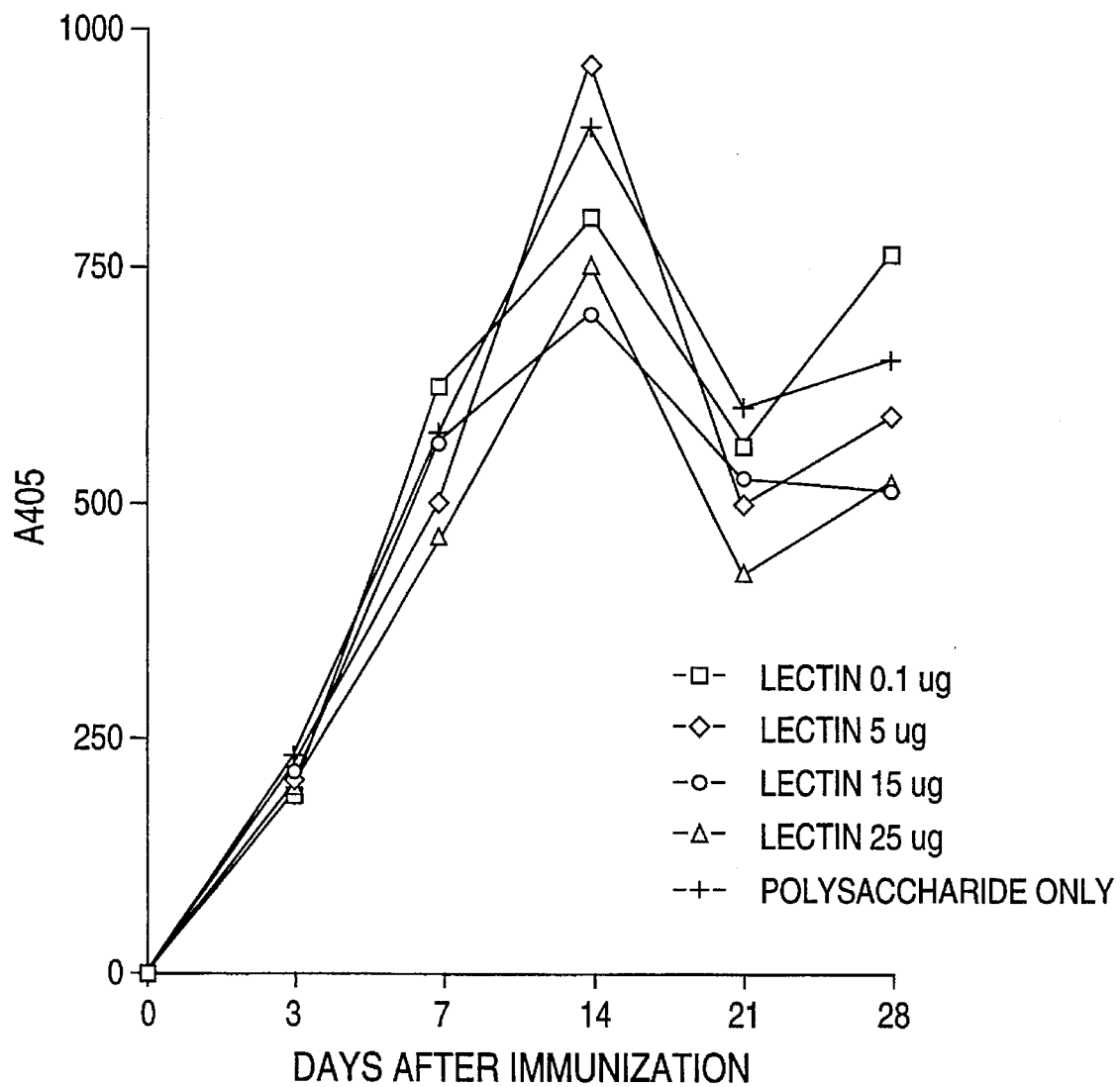
Figure 13C:
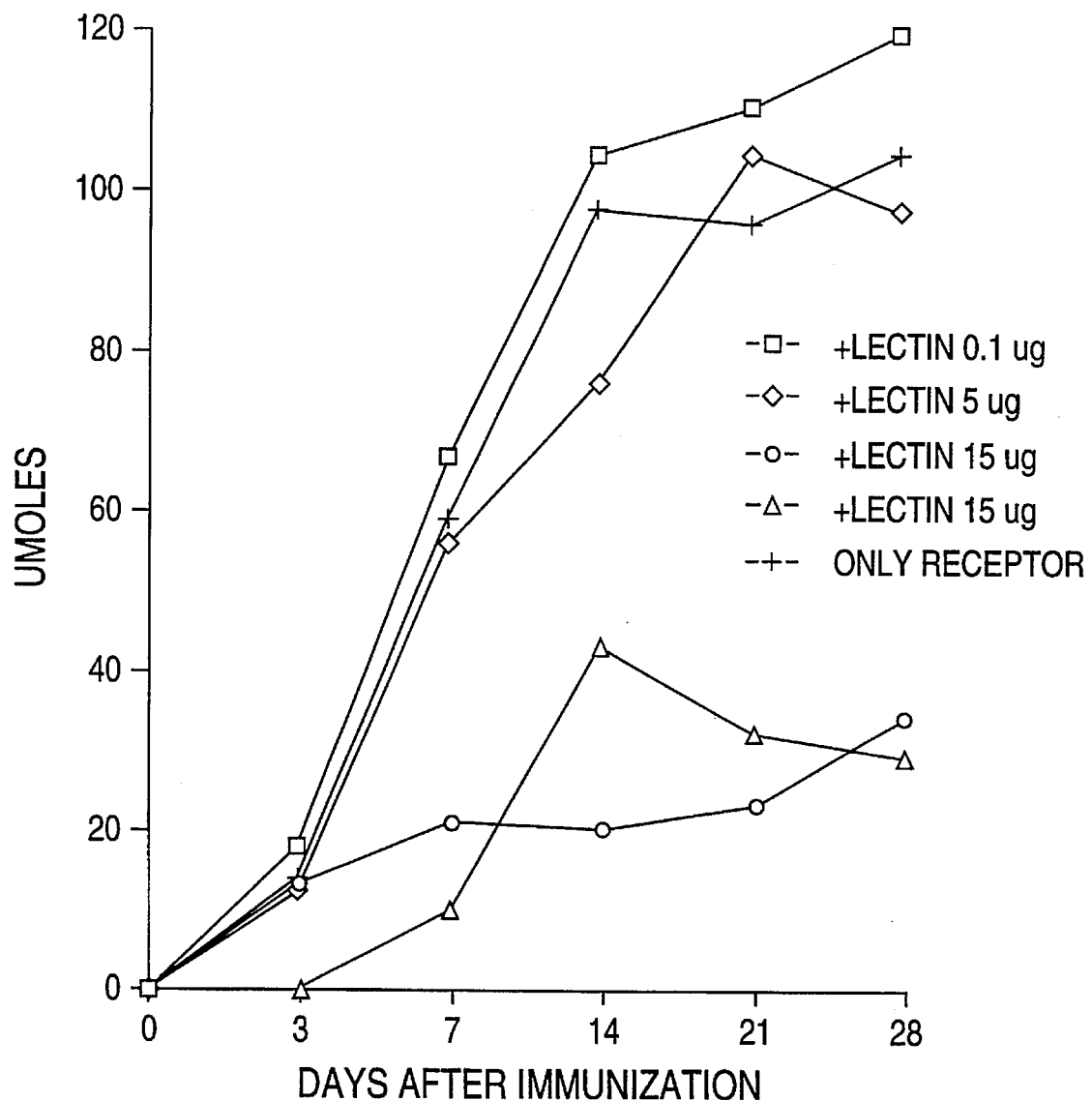
Figure 13D:
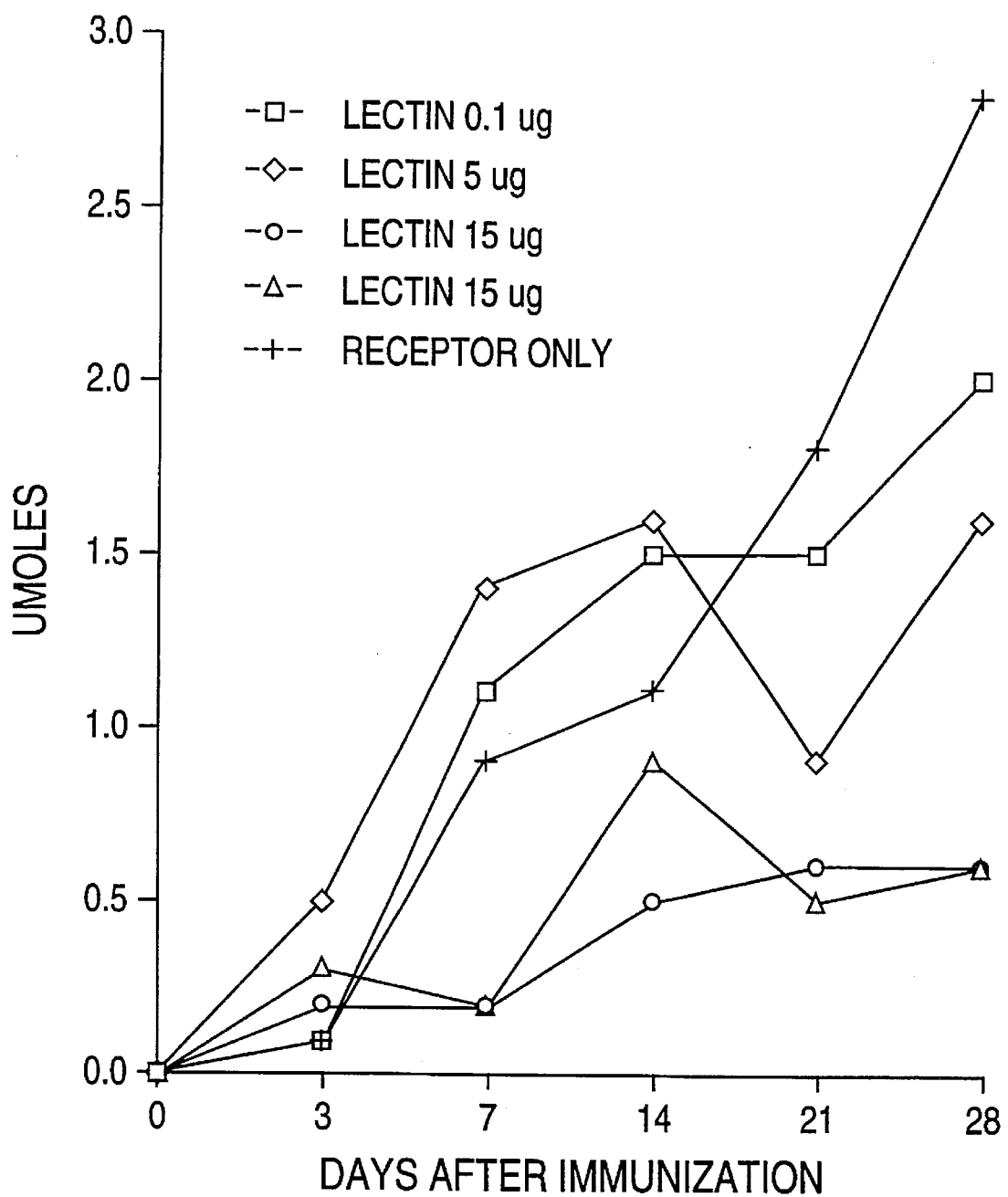

Blood was obtained after 3 days and again after 1, 2, 3 and 4 weeks and antibody levels were determined. These results are shown in FIGS. 13A, 13B, 13C and 13D. As seen in FIGS. 13A, 13C, and 13D, the primary immune response to T-dependent antigens was significantly lowered when higher concentrations of lectin were administered. Similar results were not observed for pneumococcal polysaccharide (FIG. 13B), a T-independent antigen.

EXAMPLE 10

Effect of HL-60 Lectin on Experimental Autoimmune Encephalomyelitis, An Animal Model for Multiple Sclerosis Results are shown in Tables 4 and 5 for intravenous injections of recombinant HL-60 lectin in rats. Intravenous administration of lectin when started at day 0, with additional lectin treatment at days 4 and 6, resulted in a slight delay in the onset of sickness, the sickness was less severe, the duration of sickness was shorter, and weight loss was less.

Table 5 shows that when the lectin was administered as early as three days before immunization and followed by daily injections until day 7, the development of the disease was prevented completely.

TABLE 4

| | IV Injection of Lectin and Buffer | | | |
|---|---|---|---|---|
| | Day of onset | Severity of disease | Duration (in days) | Loss of Weight(g) |
| Group I | | | | |
| 10 control rats Injected with buffer Days 0,4,6 | 14.5 | 3.2 | 4 | 30 |
| Group II | | | | |
| 10 rats Injected with 250 mcg Lectin Days 0,4,6 | 17 | 2.2 (p <.01) | 3.0 | 20 |

Disease severity on scale of 0 to 4, where 0 = death
0 = No signs of disease.
1 = Flaccid tail.
2 = Ataxia.
3 = Hind quarter paralysis.
4 = Quadriplegic/Moribund.

TABLE 5

| | IV Injection of Lectin and Buffer | | | |
|---|---|---|---|---|
| | Day of onset | Severity of disease | Duration (in days) | Loss of Weight(g) |
| Group I | | | | |
| 12 control rats Injected with buffer Days −3,−2,−1,0, 1,2,3,4,5,6,7 | 14 | 3.3 | 4.5 | 40 |
| Group II | | | | |
| 12 rats injected with 250 mcg lectin Days −3,−2,−1,0, 1,2,3,4,5,6,7 | — | 0 (p<.001) | 0 | None |

EXAMPLE 11

In Vivo Effect of Lectin-Treated Rats On Phenotypes of Selected Lymphocytes

Table 6A shows a 28% increase in the number of rat lymph node suppressor T cells (reactive with monoclonal antibody OX8, Serotec-Bioproducts, Indianapolis, Ind.) from lectin-treated animals.

Table 6B shows a 32% increase in the number of spleen suppressor T cells as well as a 19% and 24% decrease in the numbers of helper T cells (w3/25 antibody reactive, Serotec-Bioproducts) and total T cells (w3/13 antibody reactive, Serotec-Bioproducts), respectively.

TABLES 6A and 6B

In Vivo Effect of Lectin-Treated Rats on Phenotypes of Selected Lymphocytes

| Antibody | CONTROL | | | LECTIN | | | % CHANGE IN POSITIVES |
|---|---|---|---|---|---|---|---|
| | $F_L$ | % positive | % | $F_L$ | % positive | % | |
| 6A. Lymph Node Cells | | | | | | | |
| IgG | 131 | 15.9 | — | 129 | 16.4 | — | — |
| W3/13 | 443 | 99.5 | 83.6 | 442 | 99.5 | 83.1 | 0 |
| W3/25 | 216 | 78.1 | 62.2 | 230 | 76.5 | 60.1 | −0 |
| OX8 | 448 | 26.7 | 10.8 | 472 | 30.3 | 13.9 | +28 |
| OX6 | 1141 | 8.5 | 0 | 1208 | 10.0 | 0 | 0 |
| OX12 | 340 | 9.4 | 0 | 316 | 9.9 | 0 | 0 |
| 6B. Spleen Cells | | | | | | | |
| IgG | 123 | 22.5 | — | 129 | 24.3 | — | — |
| W3/13 | 334 | 98.5 | 76.0 | 311 | 85.9 | 61.7 | −19 |
| W3/25 | 195 | 79.2 | 56.7 | 161 | 67.2 | 43.0 | −24 |
| OX8 | 311 | 35.4 | 12.9 | 323 | 41.2 | 17.0 | +32 |
| OX6 | 720 | 14.6 | 0 | 375 | 15.6 | 0 | 0 |
| OX12 | 262 | 14.9 | 0 | 363 | 15.4 | 0 | 0 |

EXAMPLE 12

The results in Table 7 show that recombinant human lectin specifically reacts with human macrophages. When human blood cells were pretreated with HL-60 lectin and then stained with specific antibody (fluorescinated), no significant changes were observed for CD3+, CD4+, NK(L-A) or HLA-DR cell markers (Becton-Dickinson). The effect of lectin treatment on M1 and M3 macrophages was significant, however. The percent of positive cells was reduced by 33% and 26% respectively, suggesting an interaction between lectin and epitopes recognized by M1 and M3 antibodies.

TABLE 7

| | Control | | | Lectin | | |
|---|---|---|---|---|---|---|
| | +FL1 | +mode | percent | +FL1 | +mode | percent |
| CD3+ | 624 | 620 | 76.4 | 458 | 416 | 77.8 |
| CD4+ | 257 | 234 | 40 | 181.5 | 151 | 46.4 |
| NK(L-A) | 169 | 157 | 10.8 | 106 | 94.7 | 10.8 |
| HLA-DR | 673 | 417 | 16.3 | 614 | 432 | 13.3 |
| M1 | 345 | 323 | 79.5 | 403 | 387 | 46.1 |
| M3 | 575 | 556 | 70.7 | 549 | 517 | 45.1 |

We claim:

1. A human HL-60 lectin in purified and isolated form, said lectin having an amino acid sequence consisting of positions 2–135 in FIG. 1A; and having a molecular weight of about 14 kd, wherein said human HL-60 lectin is homogeneous using the criterion of producing a single peak when subjected to C4-HPLC, capable of binding to asialofetuin and trypsinized rabbit erythrocytes and wherein agglutination of said lectin is inhibited by thiodigalactoside and beta-lactose.

* * * * *